(12) United States Patent
De Saro et al.

(10) Patent No.: US 6,784,429 B2
(45) Date of Patent: Aug. 31, 2004

(54) APPARATUS AND METHOD FOR IN SITU, REAL TIME MEASUREMENTS OF PROPERTIES OF LIQUIDS

(75) Inventors: Robert De Saro, Annandale, NJ (US); Arel Weisberg, East Brunswick, NJ (US)

(73) Assignee: Energy Research Company, Staten Island, NY (US)

( * ) Notice: Subject to any disclaimer, the term of this patent is extended or adjusted under 35 U.S.C. 154(b) by 121 days.

(21) Appl. No.: 10/126,098

(22) Filed: Apr. 19, 2002

(65) Prior Publication Data

US 2003/0197125 A1 Oct. 23, 2003

(51) Int. Cl.[7] .............................................. G01J 3/443
(52) U.S. Cl. ................................. 250/339.07; 250/343
(58) Field of Search .......................... 250/339.07, 343, 250/352, 338.5, 574, 227.11; 266/44, 100, 265, 270; 356/313, 317, 318, 328

(56) References Cited

U.S. PATENT DOCUMENTS

| | | | |
|---|---|---|---|
| 3,935,371 A | * | 1/1976 | Camacho et al. ............. 373/18 |
| 4,928,015 A | * | 5/1990 | Butler et al. ................. 250/343 |
| 4,986,658 A | | 1/1991 | Kim |
| 4,993,834 A | | 2/1991 | Carlhoff et al. |
| 4,995,723 A | | 2/1991 | Carlhoff et al. |
| 5,223,715 A | * | 6/1993 | Taylor ......................... 250/343 |
| 5,246,868 A | * | 9/1993 | Busch et al. ................. 436/101 |
| 5,526,112 A | * | 6/1996 | Sahagen ....................... 356/72 |
| 5,664,401 A | | 9/1997 | Portrait et al. |
| 5,751,416 A | | 5/1998 | Singh et al. |
| 5,781,289 A | | 7/1998 | Sabsabi et al. |
| 5,830,407 A | | 11/1998 | Cates |
| 6,008,896 A | | 12/1999 | Sabsabi et al. |
| 6,071,466 A | | 6/2000 | Cates et al. |
| 6,221,123 B1 | * | 4/2001 | Mann, Sr. .................... 75/10.14 |

\* cited by examiner

*Primary Examiner*—Constantine Hannaher
*Assistant Examiner*—Otilia Gabor
(74) *Attorney, Agent, or Firm*—Watov & Kipnes, P.C.

(57) ABSTRACT

Apparatus and method for in situ measurements of at least one property of a liquid contained within a vessel.

70 Claims, 27 Drawing Sheets

CROSS SECTION

CROSS SECTION

CROSS SECTION

CROSS SECTION

CROSS SECTION

CROSS SECTION

CROSS SECTION

CROSS SECTION

CROSS SECTION

CROSS SECTION

CROSS SECTION

CROSS SECTION

APPARATUS AND METHOD FOR IN SITU, REAL TIME MEASUREMENTS OF PROPERTIES OF LIQUIDS

FIELD OF THE INVENTION

The present invention is generally directed to an apparatus and method for in situ, real time measurements of properties of a liquid such as, for example, a molten metal. The liquid may be stationary or in a flowing state. Real time measurements may be taken from any location including inside the liquid and on the surface of the liquid. When measurements are taken below the surface of the liquid, a stable volume of an inert gas under continuous flow may be provided at the interface of the apparatus and the liquid to enable a rapid and accurate passage of a radiation beam into the liquid to generate a detectable species which is then analyzed to determine the desirable properties. Alternatively, the apparatus may operate in a passive mode without any supplied radiation by detecting species emanating from the liquid.

BACKGROUND OF THE INVENTION

The measurement of various properties of a liquid including, but not limited to, quantitative and qualitative measurements such as concentration and composition is of critical importance in a variety of industrial applications. When a liquid is contained within a vessel, measurements can be routinely taken by obtaining a sample of the liquid and transporting the sample to a remote location such as a laboratory so that the sample may be analyzed. Quantitative and qualitative measurements can be taken at the laboratory and then transmitted back to the operator of the vessel to determine if adjustments to the composition of the liquid must be made. While instrumentation is well known in the art to measure concentration and composition of a liquid, the time it takes to make such measurements and to relay the information to the operator of the vessel can be critical to productivity as in the metal (e.g. the production of steel or aluminum) and glass industries.

As an example, closely controlling the composition of steel during its manufacture is critical to the production of quality products. It is incumbent upon the operators of the steel plant to fine tune the composition of the molten steel. Currently, samples of molten steel are taken from the furnace, transported to a laboratory where spectrometric measurements are taken that determine the elemental composition of the steel. The results of the analysis are transmitted back to the furnace operator who determines whether the actual composition of the molten steel is the same as that desired. If not, adjustments to the composition may be made by adjusting the relative amounts of the components of the molten metal.

The time it takes to complete the compositional analysis of the molten product therefore is critical to the rate of production of the desired product (e.g. steel). It therefore is desirable to employ an apparatus and method for in situ analysis of liquids such as molten metals and glasses so that adjustments to the composition of the liquid may be made in a shorter period of time than through the use of outside labs. One such approach is disclosed in Carlhoff et al. (U.S. Pat. No. 4,995,723 and related U.S. Pat. No. 4,993,834) incorporated herein by reference. These references disclose a method of analyzing elements of a molten metal by providing a stationary conduit at a side wall of the vessel containing the molten metal. A laser beam is directed into the conduit and onto the surface of the molten metal. The light generated by the plasma formed by the interaction of the laser beam and the molten metal is coupled with an optical waveguide through a lens system and then introduced by the optical waveguide into a spectrometer. The system provides for measurements of the molten metal on the surface only and does so only at a fixed point due to the stationary position of the conduit.

Another stationary conduit system is disclosed in Cates (U.S. Pat. Nos. 5,830,407 and 6,071,466) incorporated herein by reference. A stationary conduit is inserted into the bottom of a vessel containing a molten metal. The center pipe of the stationary conduit carries a transparent gas under pressure to maintain an opening in the molten metal. The gas flow has a sufficiently high hydrostatic head to prevent the molten metal from entering the conduit. A sight glass assembly enables a direct view of the molten metal and an optical sensing device such as a photometer or spectrometer is employed for determining the composition of the molten metal. Here again, measurements of the molten metal are taken from a fixed position at only one location within the molten metal.

The systems described in the above-mentioned references suffer from a number of disadvantages. These prior art systems employ stationary conduits which require all measurements to be made from a fixed location either only on the surface of the molten metal or only at one location within the molten metal. Such systems are disadvantageous because the molten metal may vary in composition within a single vessel. The accuracy employed in adjusting the composition of the molten metal depends in part on getting a highly accurate reading of the entire composition of the molten bath. If only one fixed location for analysis is provided as in the above-mentioned references, the accuracy of the analysis with respect to the entire molten metal is compromised.

Further disadvantages of the above-mentioned prior art relate to the angle at which the instruments interact with the probe. Because the molten material is of higher density than the gas, the device disclosed in Carlhoff et al., cannot sustain a static bubble of gas for making measurements. The heavier molten material will flow into the hole in the furnace wall displacing any gas. Therefore, gas must be flowing continuously in order to keep the molten material out of the instrument. This continuous flow will result in a non-stationary interface between the gas and the molten material, greatly complicating the measurement process, which is most accurate when the interface is stationary so that the optics are in focus. Since constant pressure is required to keep the molten material out of the device, the loss of gas pressure due to for example, a leak in the gas supply line, may adversely affect the desired measurements and may result in damage to the instruments.

The device disclosed in the Cates references has similar disadvantages. While a vertical orientation can maintain a static surface, if pressure is lost, the device will be destroyed and the molten material lost, just as in the case of Carlhoff et al. Also, while the vertical column of gas can be stationary in Cates, it is unstable, particularly if some of the gas is released into the bath due to a disturbance of sufficient magnitude, the remainder of the gas is likely to follow, and molten material will flow into the tube.

A further disadvantage of Cates concerns the required access from the bottom of the furnace. It is typically very difficult to gain access to the bottom of commercial furnaces because of the weight of the furnace. Also, there is the potential for a disastrous leak of molten material onto the factory floor with a port located on the bottom of the furnace. When the port is on the side, material will leak out only until the level of molten material in the vessel falls below the level of the port. With the port positioned on the bottom of the vessel, and the column containing the gas extending only a short distance into the furnace, nearly the entire volume of molten metal contained in the furnace can leak out if there is a loss of gas pressure.

Another disadvantage in the Cates and Carlhoff et al., systems relates to the location where analyses are performed. Carlhoff et al., samples the molten material at the wall of the furnace, and Cates samples the molten material near the bottom of the furnace. These locations may contain molten material that is not representative of the bath as a whole. When the furnace operators introduce alloying elements into the bath, they attempt to mix them thoroughly throughout the bath. However, it is most difficult to ensure thorough mixing of the ingredients close to the side walls of the furnace where it is difficult to introduce mechanical agitation. If the alloying elements are diffusing throughout the bath, it wall take the longest period of time for them to reach the walls. If the melt is poured before diffusion is complete, sampling near the walls will not be representative of the bath as a whole. Also, in the case of molten glass there are large thermally generated currents, such as rising pockets of hotter material and descending flows of cooler material. These rising and falling currents tend to prevent or render the production of the homogenous melt more difficult.

Other approaches to making quantitative and/or qualitative measurements of a metal employ laser induced breakdown spectroscopy (LIBS) systems. Such systems generally provide an apparatus for in situ real-time spectroscopic analysis of a material through the employment of laser pulses of sufficient power to irradiate a representative quantity of a heterogeneous sample to the extent that it forms a plasma. The plasma is composed of a small amount of the material which has been vaporized and ionized by the laser pulses. In the plasma, the molecules of the material are dissociated and the atoms are excited into charged states. As the plasma cools, the charged atoms (ions) emit electromagnetic waves in wavelengths specific to the atom of the particular element. By observing the electromagnetic radiation with a spectrometer capable of resolving the different wavelengths, the elements in the radiated sample can be identified. Quantifying the intensity of the radiation and comparing it to reference samples, and/or through calculations using various atomic constants, the concentration of the atomic elements in the material can be ascertained.

Examples of such systems used to analyze solid samples are disclosed in Sabsabi et al., (U.S. Pat. Nos. 5,781,289 and 6,008,896). Eivindson (U.S. Pat. No. 5,664,401) analyzes molten metal through this method by applying a LIBS system to the gas above the surface of the molten material and inferring the composition of the melt from the measured composition of the gas. Singh et al., (U.S. Pat. No. 5,751,416) describes a method of analyzing a liquid material directly using a LIBS system but only on the surface of the liquid. Each of the above-mentioned references is incorporated herein by reference.

Kim (U.S. Pat. No. 4,986,658), incorporated herein by reference, describes a method of analyzing molten metals below the surface of the melt using a LIBS system. The reference design suffers from a number of drawbacks. Firstly, the expensive components of the device (i.e. the spectrometer and the laser) are placed very close to the furnace. In the event of an accident in which these components either fall into the furnace or otherwise come into contact with the molten metal or are exposed to temperatures above the tolerance threshold of the components (e.g. a failure in the cooling system), the investment in the instrument is lost. This danger complicates the reference design, requiring the use of heat shields and coolant systems. This complexity adds to the cost of the system and increases the number of subsystems that can fail, leading potentially to a loss of the equipment. Also, the probe is limited to a few centimeters below the melt surface so as to void any floating slag. The system is also incapable of being immersed to any appreciable extent within the furnace.

Another consequence of the reference design is the limited number of locations the melt can be sampled. Because of the placement of the spectrometer and laser just above the molten material, the device of the reference '658 patent can not probe into deeper locations of the melt without substantially changing the design, such as lengthening the exterior of the probe and changing the focal lengths of the optical components. Also, the probe cannot be inserted at an angle other than vertical, further limiting the applicability of the design only to furnaces that have access from the top of the furnace. As detailed above, sampling the molten material at multiple locations may result in substantially better analysis of the melt.

Another drawback of the '658 patent device is that it prevents deployment of multiple probes throughout a metal manufacturing facility. By coupling the laser and spectrometer to the probe housing, deploying multiple probes would force the plant operator to purchase many lasers and spectrometers, a prohibitive expense.

The reference device is further disadvantageous because it does not flow inert gas into the molten material. There are two benefits to flowing inert gas into the melt. First, the inert gas can locally stir the melt so that each laser pulse does not result in an analysis of the same material. Second, the flow of inert gas can remove contaminants from inside the molten material. This occurs in two ways. Undesirable gases dissolved in the melt are mixed into the inert gas as it rises and are thereby removed from the melt. Also, contaminants that would ordinarily float to the top of the melt to be skimmed off are agitated by the bubbles and rise more quickly than they would otherwise. The practice of using an inert gas to remove contaminants is well known to those versed in the art of molten metal production.

It would therefore be a significant advance in the art of performing in situ real time measurements of a liquid if an apparatus could be provided which is capable of measuring at least one property of a liquid regardless of whether the liquid is stationary or flowing, and is mobile, so that the apparatus can rapidly sample the liquid at multiple locations within the liquid or on the surface thereof. It would be a further advance in the art to provide an apparatus which can be inserted into the liquid at different angles with respect to the surface of the liquid and which neither the liquid or the components of the apparatus will be lost if there is a system failure.

It would be a still further advance in the art to provide an apparatus and method for making such measurements in which there is greater efficiency in the use of relatively expensive components (e.g. laser) and the elimination of unnecessary duplication of such components.

It would be an additional advance in the art to provide an apparatus and method for making such measurements in which if the apparatus is submerged in the liquid, the supply of inert gas to the liquid may assist in a) purifying the liquid, b) stirring the liquid so that a more representative sample of the liquid is analyzed, and c) preventing interference with the measurements by not generating bubbles of gas within the liquid that interfere with the sensor's operation.

SUMMARY OF THE INVENTION

The present invention is generally directed to an apparatus and method for in situ, real time qualitative and/or quantitative measurements of properties of a liquid such as, for example, a molten metal. The liquid may be stationary or in a flowing state. The invention is capable of taking such measurements from the surface of the liquid and from any location inside the liquid. When used below the surface of the liquid, a stable volume of an inert gas under continuous flow may be provided at the interface of the apparatus and the liquid to enable a rapid and accurate passage of a radiation beam into the liquid to generate a detectable species, which is then analyzed to determine the desired properties. The apparatus may, instead of a stable volume of inert gas, employ a window as a barrier to the liquid entering the apparatus. Alternatively, the apparatus may be passive, detecting species emanating from the liquid without any radiation supplied by the apparatus.

In one aspect of the present invention, there is provided:

An apparatus for measuring at least one property of a liquid at or below the surface of the liquid comprising:
a) a housing having a forward end;
b) at least one probe assembly at the forward end of the housing, said probe assembly comprising an inert gas generating means comprising a source of inert gas, a conduit for channeling the inert gas to the forward end of the housing and means for providing, under flow from the source of inert gas, a stable volume of inert gas at the interface of the forward end of the housing and the liquid;
c) a radiation beam assembly comprising means for generating a beam of radiation sufficient to vaporize a portion of the liquid into a detectable species, means for transmitting the radiation beam through the forward end of the housing to the interface of the liquid and the stable volume of inert gas; and
d) detection means for receiving the detectable species and for detecting from said detectable species at least one property of the liquid.

Methods of measuring properties of liquids at or below the surface thereof using the apparatus are also encompassed by the present invention.

In another aspect of the invention, a window is provided at the end of the probe assembly through which the laser beam is transmitted thus eliminating the need of providing at stable volume of gas at the interface with the liquid to be analyzed.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

Figure 1:
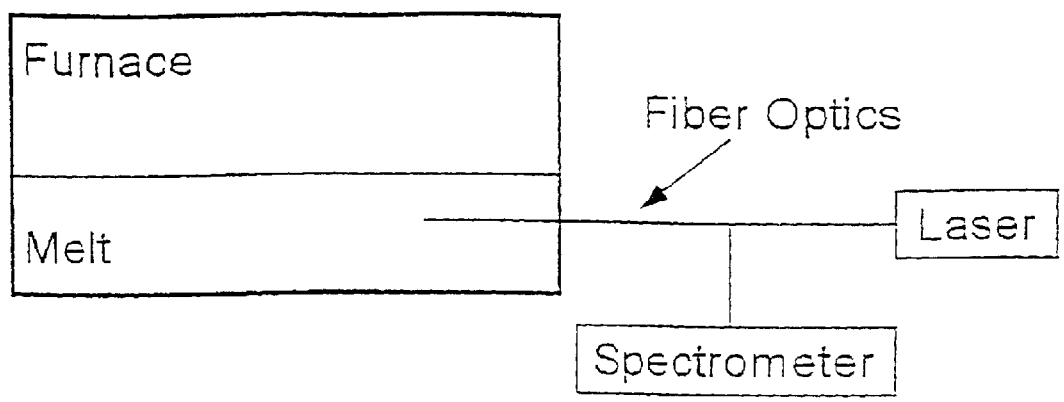
FIG. 1 is a schematic view of a known laser induced breakdown spectrometric system for analyzing a molten material in-situ.

The present invention is directed to a device for in situ, real time analysis and measurements of at least one property of a liquid which may be stationary such as in a vessel or flowing such as a pour of a molten metal from a vessel containing the same. The term "liquid" as used herein refers to all types of liquids whether clear or opaque liquids regardless of temperature. Such liquids can include, but are not limited to, molten materials such as molten metals and molten glass, as well as solutions, suspensions, emulsions and the like. The present invention provides a probe assembly that may obtain such analyses and measurements from the surface of the liquid or from any position within the body of the liquid since the probe assembly can be immersed in the liquid.

The apparatus of the present invention may be mobile and therefore can be moved rapidly from one position to another to obtain spatially distributed measurements in a short period of time to enable the determination of properties of the liquid including, but not limited to, composition and concentration that cannot be obtained with the same rapidity and accuracy of typical prior art devices due to their lack of mobility. In one embodiment of the invention as discussed hereinafter, the apparatus has one or more probe assemblies capable of taking surface and/or subsurface measurements at the same time. When submerged, the apparatus of the present invention may employ a stable interface between the probe assembly and the liquid via a supply of relatively cool inert gas. The supply of cool gas controls the temperature of the apparatus and thereby enables in situ, real time analysis of the liquid without damage to the radiation beam transmission assembly which is used to transmit and/or generate, and/or detect a detectable species of the liquid for analysis.

The stable interface between the probe assembly and the liquid is a stable volume of inert gas which is generated by a flow of the inert gas, typically a continuous flow, and a pressure control assembly which ensures the stability of the volume of gas at the interface. The apparatus and method employing this embodiment of the invention ensures that the functions of the components that generate and/or detect the detectable species from the liquid and the components themselves, are not adversely affected by virtue of their being in proximity to the liquid. This can be a significant advantage when the liquid is a molten material. This protection is facilitated because the stable volume of gas is formed from a supply, preferably continuous supply, of relatively cool gas. The gas is thus prevented from reaching extreme temperatures due to its proximity to the molten material. Furthermore, as the temperatures of the gas rises it is removed from the system and replaced with cool gas so that the overall temperature of the gas in proximity to temperature sensitive components of the apparatus is below a damage threshold. Consequently, the components of the apparatus are protected from damage, thus ensuring their proper operation.

An additional advantage of utilizing an inert gas as described above occurs when the apparatus is immersed in the liquid to analyze the liquid at a location beneath the surface thereof. As the apparatus is lowered into the liquid, the local fluid pressure increases at the tip of the apparatus where the measurement takes place. If the flow of gas is maintained, there is sufficient pressure to keep the molten material from entering the probe assembly and the location of the stable interface is kept at a constant volume. By contrast, if a static bubble of gas is used, then the molten material may easily enter the apparatus if the gas pressure is not properly increased. Similarly, when the probe assembly is raised, and the local fluid pressure at the tip of the probe assembly drops, high pressure gas in a static bubble may escape out the bottom of the probe assembly, potentially allowing the molten material to enter and damage the probe assembly. A flow of gas in accordance with the present invention provides compensation for changes of pressure and therefore prevents damage to the apparatus.

In an effort to overcome the disadvantages of the prior art systems, an embodiment of the present invention is directed to an apparatus and method for analyzing liquids including molten materials such as molten metals and molten glass in which a stable interface between a probe assembly and a liquid is provided to ensure against distortion of any radiation beam used to generate a detectable species due to loss of focus, and the rapid and accurate analysis of the detectable species which is generated thereby. The present invention also provides for rapid measurements at multiple locations including multiple measurements simultaneously. As a result of the present invention, a profile of at least one property of the liquid including, but not limited to, composition, concentration and the like, can be generated over essentially the entire body of the liquid and changes over time can be continuously monitored. Because of the improvements associated with the present invention, it is now possible to provide measurements of flowing liquids not just a passive liquid contained within a vessel that may have a significant impact on a variety of industries including the production of metal and glass from corresponding molten materials.

Figure 2:
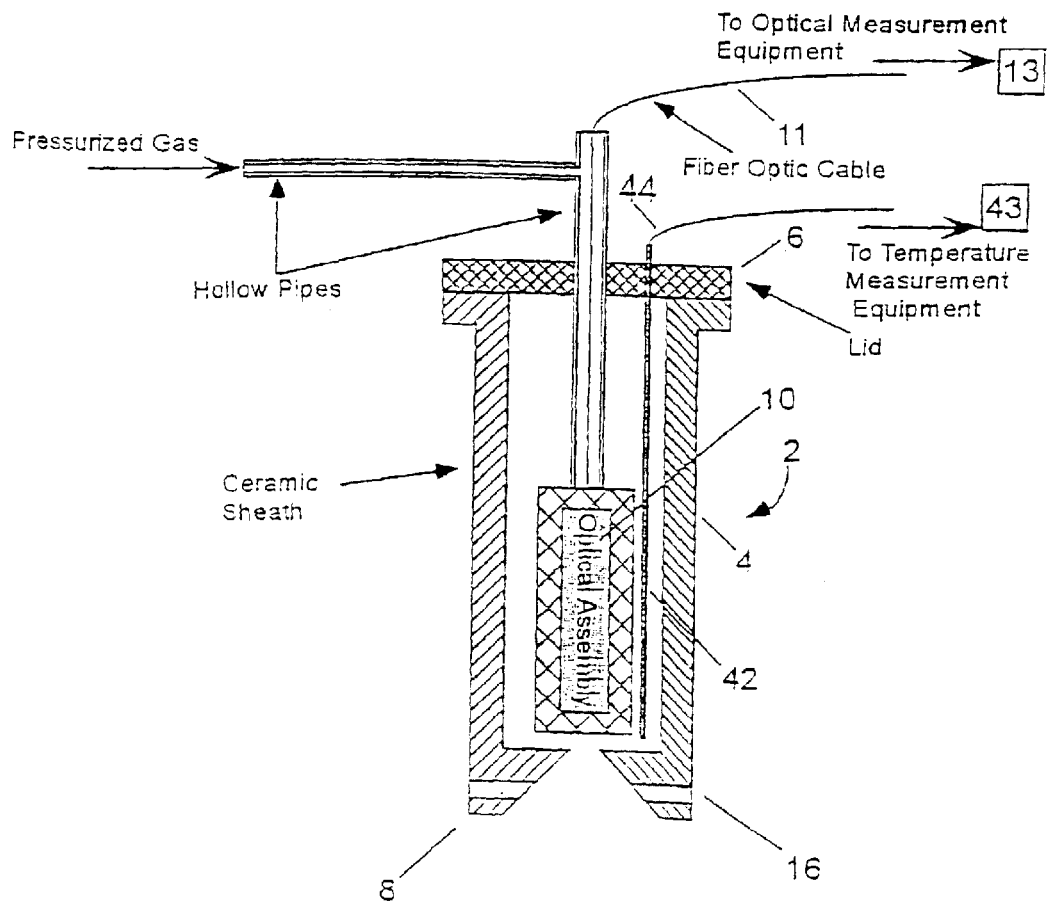
FIG. 2 is a cross-sectional view of a probe assembly in accordance with an embodiment of the present invention.
Figure 3:
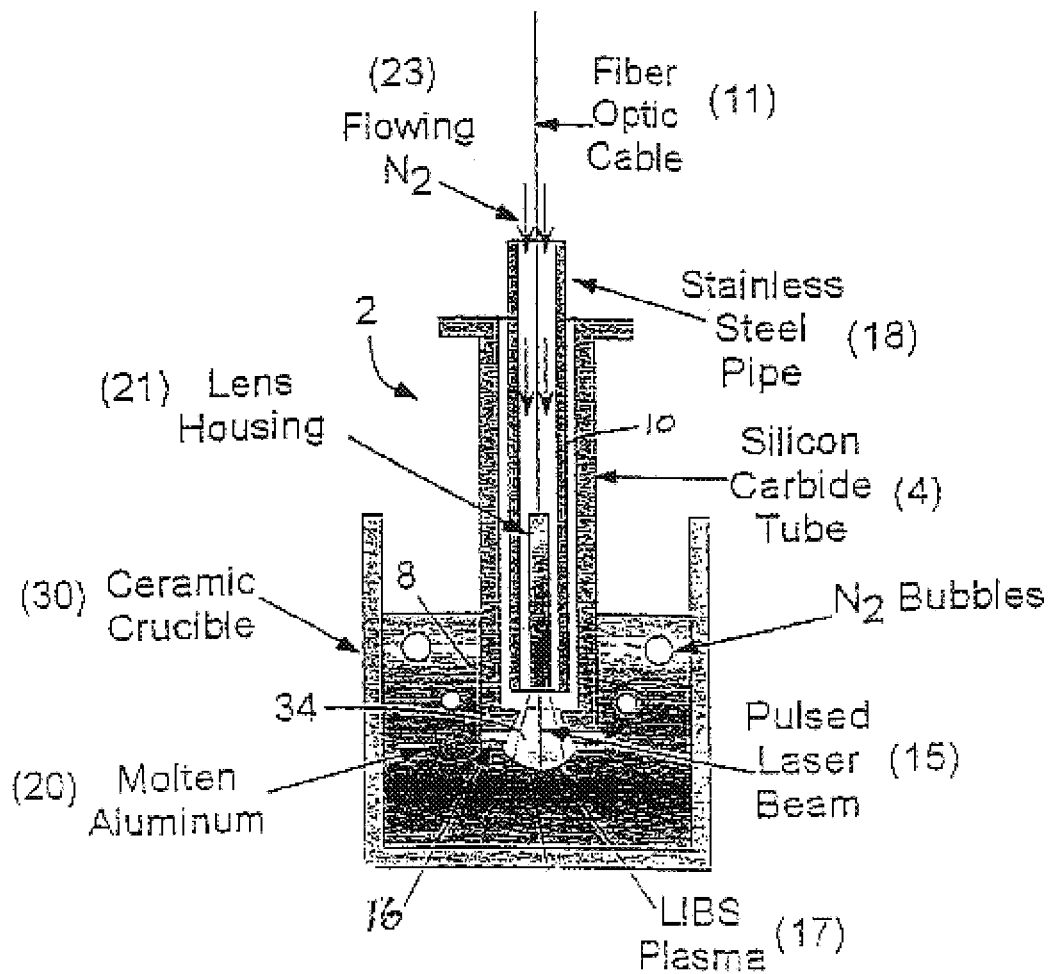
FIG. 3 is a cross-sectional view of an embodiment of a probe assembly in accordance with the present invention immersed in a vessel containing a liquid.

Referring to the drawings and first to FIGS. 2 and 3, there is shown an embodiment of the present invention for detecting at least one property of a liquid contained either within a vessel, whether in a stationary or flowable condition. As shown specifically in FIG. 2, there is provided a probe assembly 2 of the present invention comprised of a housing 4 having a rearward end 6 and a forward end 8. In this embodiment of the invention, the forward end 8 forms the stable interface with the liquid as hereinafter described.

Figure 18:
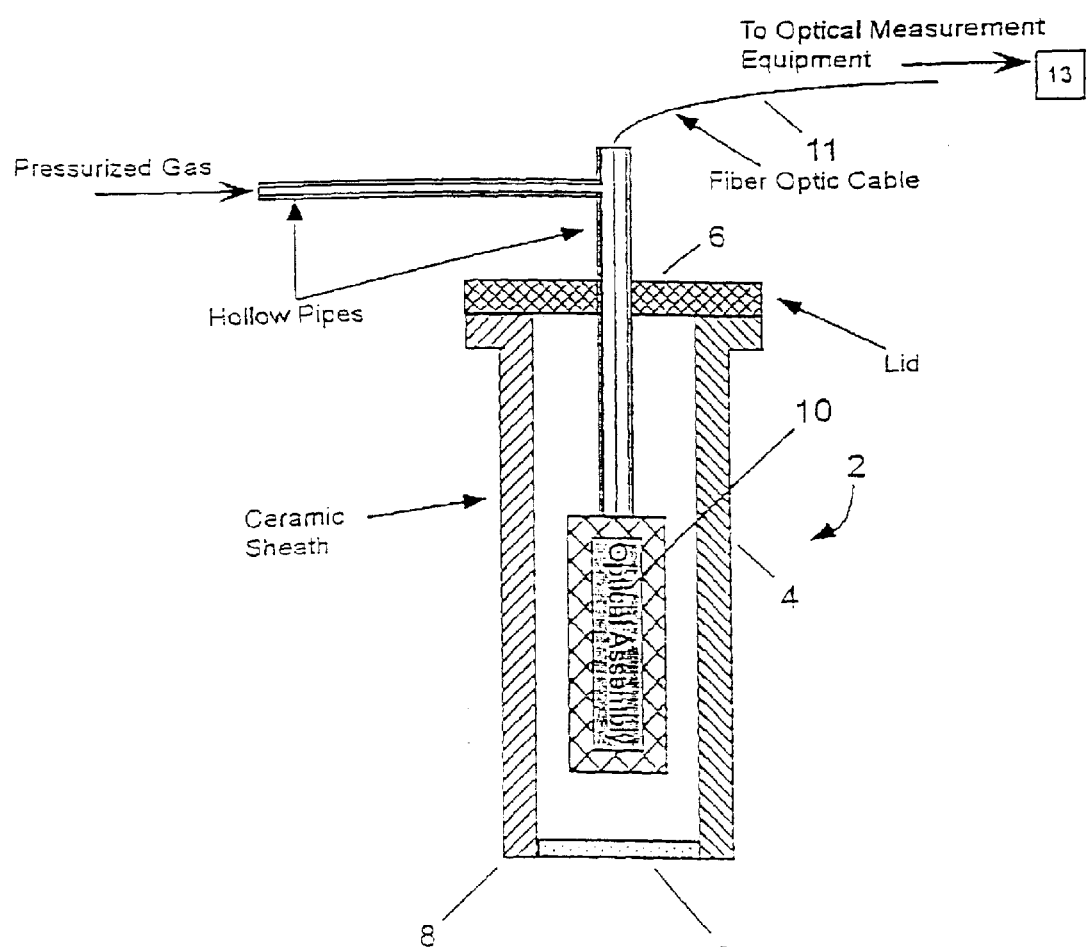
FIG. 18 is a cross-sectional view of another embodiment of the apparatus of the present invention in which a window is employed at the forward end of the apparatus in place of the stable volume of inert gas.

Alternatively, the invention may employ a window 9 at the opening at the forward end of the apparatus in place of the stable gas-liquid interface as shown specifically in FIG. 18. This configuration may be employed in the embodiments shown in FIGS. 13, 24, 25 and 27 as discussed hereinafter.

Contained within the housing 4 is a radiation beam assembly 10 which may comprise a laser beam transmission and/or focusing assembly such as a LIBS system (See prior art FIG. 1), a sonic beam transmission and/or focusing assembly (including ultrasonic beams, see FIG. 13), or an assembly capable of transmitting and/or focusing another type of radiation such as electromagnetic radiation (e.g. x-rays, see FIG. 24) from various parts of the spectrum. The assembly 10 receives the radiation beam from a location inside or outside the housing 4 (outside the housing as shown in FIG. 2) through a suitable cable assembly 11, transmits the radiation beam to the liquid-gas interface if present, and directs or focuses the beam, if necessary, to produce a detectable species for measuring at least one property of the liquid. The radiation emanating from the detectable species is collected by the radiation beam assembly 10 and transmitted out of the probe assembly 2 to a device shown generally by the numeral 13 responsible for performing the analysis of the liquid as explained in detail hereinafter.

Alternatively, the present invention may operate in a manner in which it does not deliver any radiation, but instead only performs the collection task described above such as described in connection with FIG. 13 hereinafter.

Figure 25:
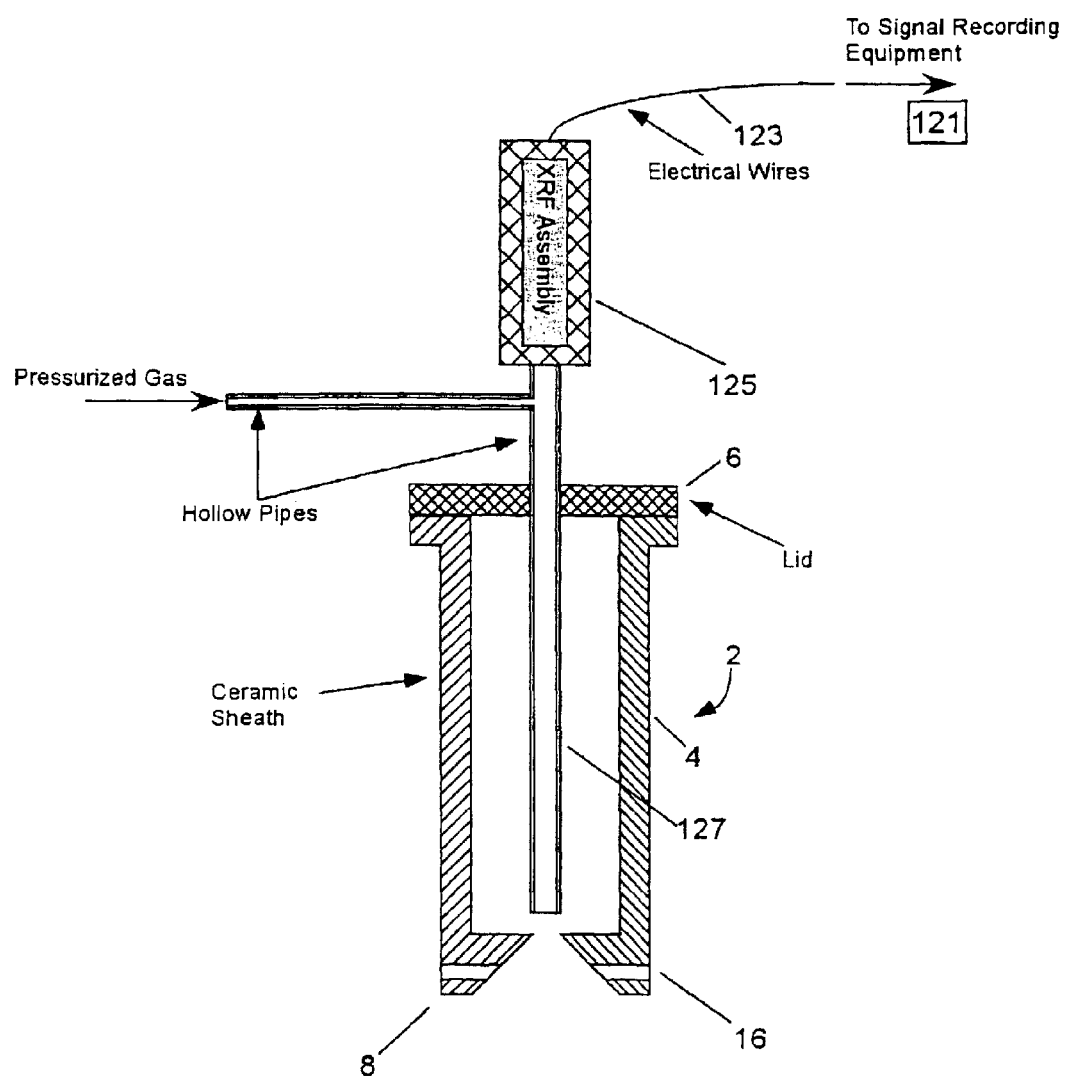
FIG. 25 is a cross-sectional view of a further embodiment of the invention similar to FIG. 24 with the x-ray fluorescence assembly positioned outside the probe assembly.

Alternatively, the radiation beam assembly 10 or assemblies for generating, transmitting, collecting, and/or focusing the radiation may extend from inside the housing 4 to outside the housing 4 such as disclosed in FIGS. 3 and 25.

In certain situations, it may be advantageous to include the radiation beam assembly, and/or the analysis assembly inside the probe. In one embodiment of the invention, the radiation beam assembly 10 is a laser beam generating assembly known to those of ordinary skill in the art, such as that disclosed in Kim (U.S. Pat. No. 4,986,658), incorporated herein by reference.

As best shown in FIG. 3, in one embodiment, a laser beam generating beam assembly 10, in concert with a fiber optic cable and/or another light transmission apparatus 11, delivers a pulsed laser beam 15 with sufficient power to perform a LIBS (laser induced breakdown spectroscopy) measurement method on the liquid 20 (e.g. molten aluminum) through the formation of a LIBS induced plasma 17 as previously described. The radiation beam assembly 10 known to those skilled in the art, is contained within its own housing 21 and transmits the pulsed laser beam 15 and focuses it on the gas liquid interface shown generally by the numeral 34. The laser beam 15 energizes and vaporizes a portion of the liquid at the interface 34 to produce a plasma plume 17 having an elemental composition representative of the elemental composition of the liquid. Shortly after the termination of the laser pulse, typically lasting up to about 1000 nanoseconds, reversals in the spectrum of the plasma plume 17 are caused by absorption of radiation emitted by the hotter inner portion of the plasma plume to relatively cooler outer portions. The radiation emitted by the outer portion is then measured during a short time window by means of a spectrometer, radiometer, or other device appropriate for the type of emitted radiation, which may be located within or outside the probe assembly. Other methods of generating a radiation beam to contact the liquid to produce a detectable species for analysis are well know to those of ordinary skill in the art and are described hereinafter.

In accordance with an embodiment of the present invention, the forward end 8 of the housing 4 is provided with a nozzle assembly which is capable of forming a stable interface in the form of a stable volume of an inert gas between the probe assembly 2 and the liquid under temperature controlled conditions.

Figure 4A:
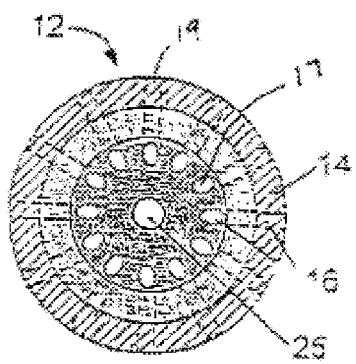
FIG. 4A is bottom view taken in cross-section of the forward end of the probe assembly in accordance with the embodiment of the present invention shown in FIG. 3.
Figure 4B:
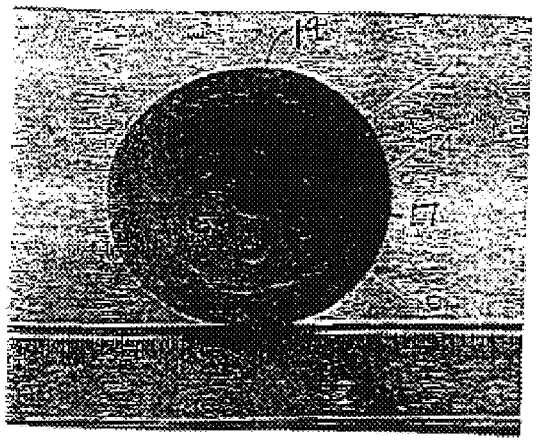
FIG. 4B is a bottom view of the forward end of the probe assembly in accordance with another embodiment of the present invention.
Figure 4C:
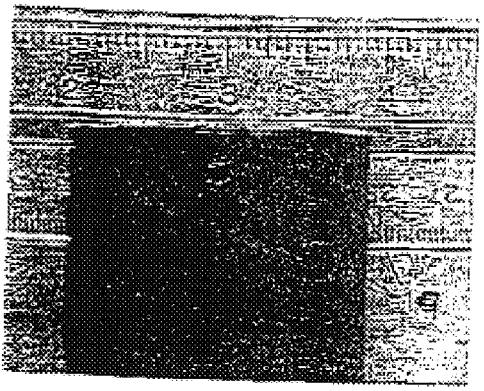
FIG. 4C is a side view of the forward end of the probe assembly shown in FIG. 4B.

The nozzle assembly is best shown in connection with FIGS. 4A–4C. The nozzle assembly 12 includes a bottom portion 14 having at least one, preferably a plurality of spaced apart channels 16. As best shown in FIG. 4B the channels 16 have a first opening 17 in the bottom portion 14 and a second, remote opening 19 in the side of the bottom portion 14. Each of the channels 16 enables an inert gas from a source 23 (See FIG. 3) to travel through the housing 4 via conduit 18 to exit the opening 25 and form a stable volume interface with the liquid. The gas then flows through the channels 16 and into the molten liquid via the second openings 19, if the openings 19 are below the surface of the liquid. The inert gas is provided through the channel 16, in a manner that provides sufficient back pressure to maintain a stable volume of the inert gas at the interface between the probe assembly 2 and the liquid. For example, if a probe is immersed into a tank of molten aluminum that is 100 cm deep, then the pressure at the bottom of the tank is approximately 1.25 times the pressure at sea level. The inert gas must be provided at a greater pressure (i.e. >1.25 times the pressure at sea level) if the forward end of the probe is to be positioned near the bottom of the tank. Maintenance of a desired pressure may be facilitated by providing a concave shape to the bottom portion 14 as specifically shown in FIG. 4B of the nozzle assembly 12 in proximity of the channels 16. In particular, the probe assembly 2 in this embodiment faces downward in the liquid which enables the build-up of inert gas at the interface.

In operation, an inert gas is fed via the conduit 18 under pressure through the nozzle assembly 12 and out the opening 25. The pressure of the inert gas is sufficient to form a stable volume of the inert gas at the interface of the liquid. Once a stable volume is obtained, gas continues to enter through the opening 25. At the same time, some of the gas which has experienced a significant increase in temperature if the liquid is a molten material, enters the channel 16 through the first opening 17 and exits via the second opening 19. Because the side openings 19 are slightly elevated in the liquid relative to the bottom portion 14 of the probe assembly, the local fluid pressure is slightly lower at the side openings 19 as compared to the most forward surface or tip of the probe assembly. This slight pressure differential is sufficient to direct the flowing gas out of the side openings 19. The open chamber at the tip of the probe is therefore filled with gas at the local fluid pressure of the tip, creating a stable gas-liquid interface amenable to taking measurements of the liquid. When the probe assembly is raised or lowered the rate of flow of gas may be altered through the side openings 19 to equalize the gas pressure at the tip with the local liquid pressure to thereby maintain the stable liquid-gas interface. In order to ensure sufficient pressure to maintain a flow of inert gas, a flow monitoring device (not shown), commonly known to those versed in the art, may be necessary to adjust the gas pressure higher so that the flow of inert gas is not stopped.

In accordance with a preferred embodiment of the present invention, the inert gas is under a continuous flow into the stable volume via the opening 25 and away from the stable volume via the channels 16, in part, to prevent the inert gas from undergoing a dramatic temperature change. This is particularly important when the liquid is at a very high temperature such as molten metal or molten glass. By maintaining a continuous flow of the inert gas, the temperature of the inert gas remains at a relatively constant and relatively cool temperature, which prevents the radiation beam assembly from becoming exposed to excessive heat which can result in a distortion of the radiation beam and/or damage to the assembly itself.

Figure 22:
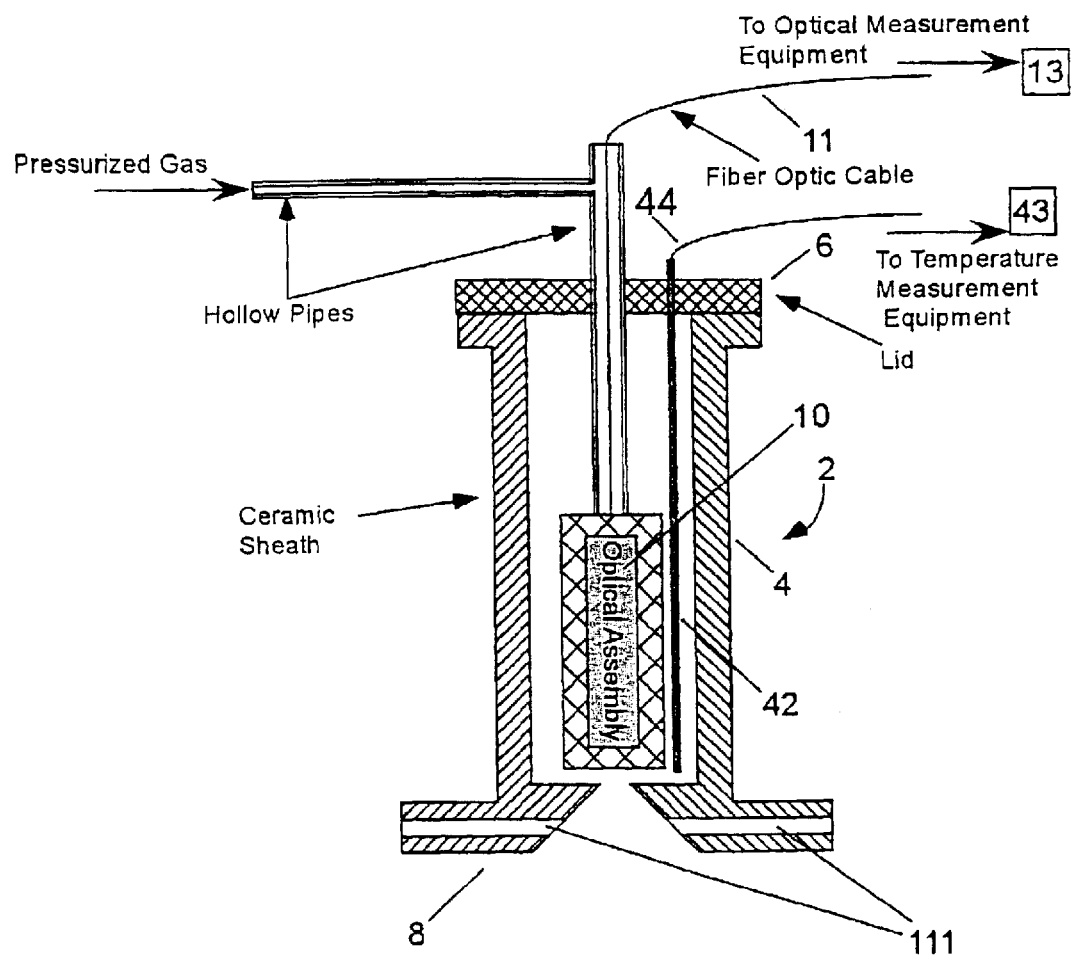
FIG. 22 is a cross-sectional view of a further embodiment of the invention employing extended passages for delivering the flowing inert gas into the liquid.
Figure 23:
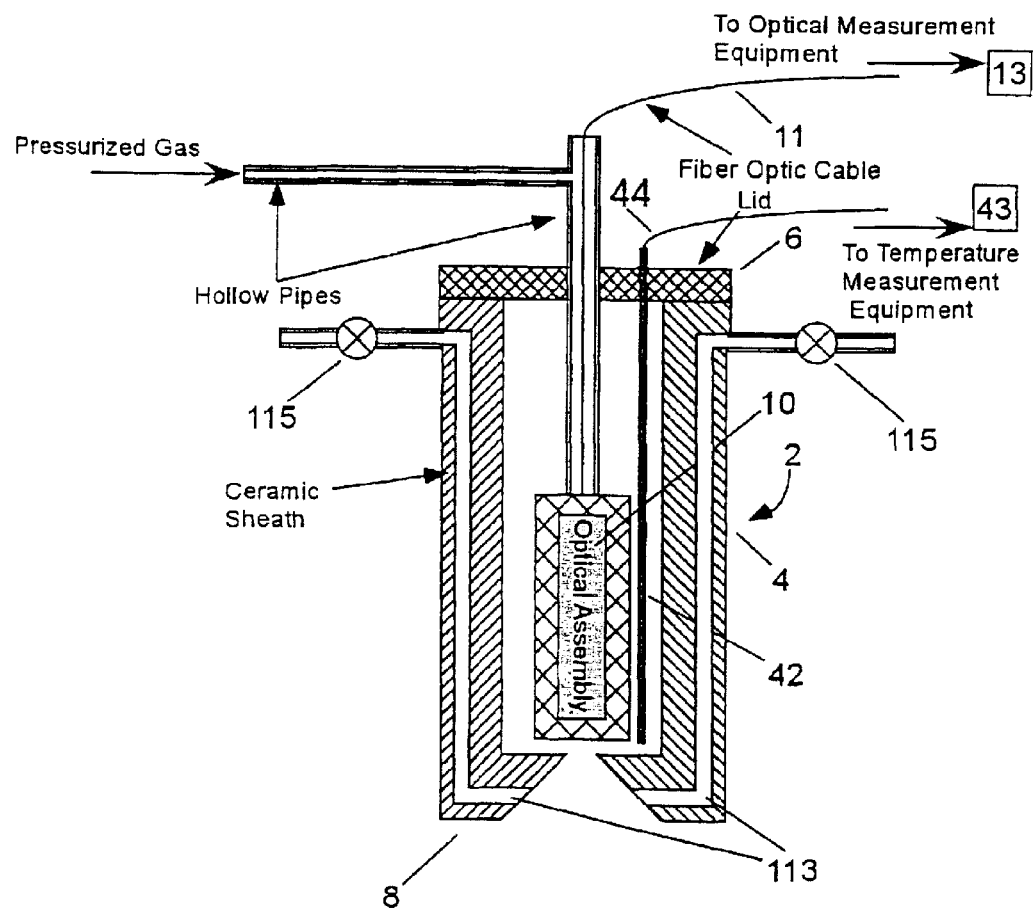
FIG. 23 is a cross-sectional view of a further embodiment of the invention employing extended passages for delivering the flowing inert gas from the forward tip of the probe assembly to the surface of the liquid.

The channels 16 may extend beyond the main body of the probe assembly, as shown in FIGS. 22 and 23. Gas bubbles exiting the channels 16 may agitate the liquid-gas interface to a degree that interferes with the desired measurement of the liquid. As shown in FIG. 22, the channels 111 may extend a distance away from the measurement location in order to minimize the effects of the bubble wakes on the liquid-gas interface. The channels 111 may be horizontal as shown, or they may be angled upwards towards the surface of the liquid.

Another embodiment is shown in FIG. 23, where the channels 113 extend all the way to the liquid surface. In this embodiment, all the gas exits the liquid without bubbling. Sufficient care must be taken in this configuration so that sufficient pressure exists at the liquid gas interface at the forward end of the probe assembly 8 to prevent the liquid from flowing therein. Because this embodiment does not compensate for depth changes, valves 115 limiting the flow of air out of the channels 113 may be employed to maintain an appropriate pressure level unless the channels themselves are of the design that constricts the gas flow sufficiently to perform the same function. Designing such channels and/or using valves to properly constrict flow to maintain pressure is within the knowledge of those versed in the art.

Figure 17:
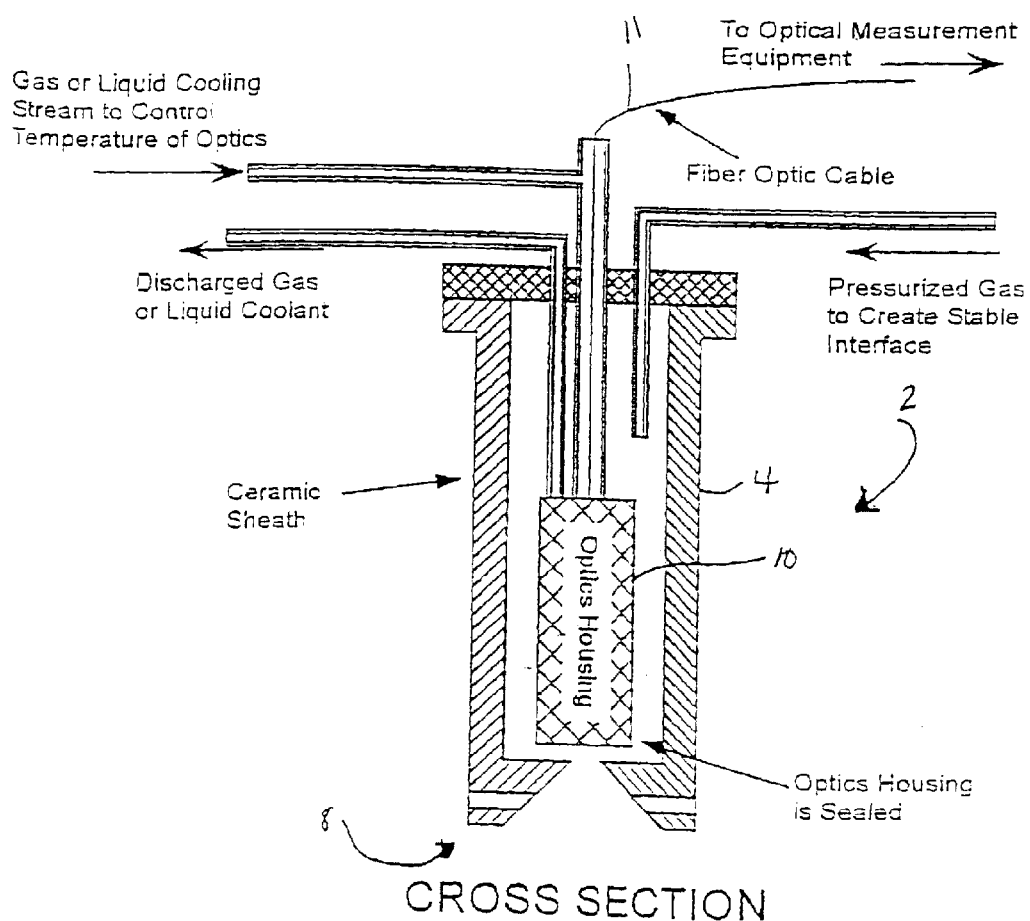
FIG. 17 is a cross-sectional view of another embodiment of the apparatus of the present invention in which a flow of gas or liquid, separate from the gas used to maintain the stable volume at the forward end of the apparatus, is used to maintain the temperature within the apparatus at operable levels.

Two gas streams at least one of which is comprised of an inert gas, or one liquid stream and one inert gas stream, can be used in place of the single inert gas stream. As shown in FIG. 17, a piping arrangement inside the probe assembly provides for the second gas stream or the liquid stream to flow around the temperature sensitive components of the probe assembly and exit the probe assembly either inside or outside the liquid, providing better protection against heat damages than can be provided by a single gas stream. If a liquid such as water is used in place of one of the gases, the water is used for cooling purposes, while the gas may be used to create the stable interface.

The stability of the volume of inert gas which serves as the interface 34 between the probe assembly 2 and the liquid 20 (see FIG. 3) and the maintenance of relatively low temperatures of the same is the result of providing a continuous flow of gas through an exit port 25 and spaced apart channels 16. The inert gas that escapes to the liquid 20 through the channels 16 is continuously replenished by a fresh supply of inert gas through a port 25. As used herein the term "stable volume" shall mean that there is a balance between incoming fresh inert gas entering through the opening 25 and escaping inert gas through the channels 16 such that at any measured period of time a fixed volume of inert gas at the interface 34 is maintained. Thus, the nozzle assembly 12 facilitates the presence of a stable volume of inert gas by the volume balance established between incoming inert gas through the conduit 18 and the release of the inert gas through the channels 16.

Figure 9:
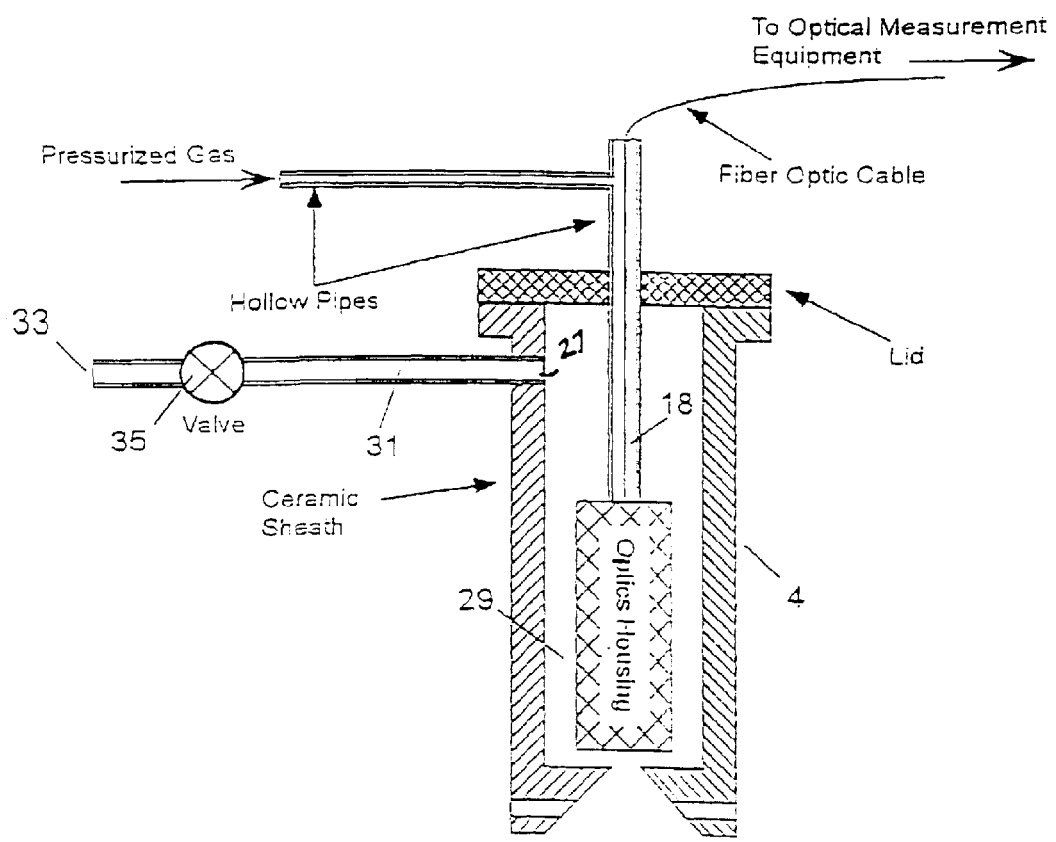
FIG. 9 is a cross-sectional view of another embodiment of the apparatus of the present invention employing a valve for the release of a pressurizing gas to the atmosphere when the gas is present in excessive quantities for the purpose of maintaining a stable volume of gas at the forward end of the apparatus.

Alternatively, some of the gas that enters via conduit 18 may exit from a port 27 in the housing 4, as shown in FIG. 9. In particular, the excess inert gas travels upwardly through the housing 4 via a pathway 29 circumscribing the probe assembly 2 and enters the exit port 27 where it travels through a conduit 31 to an exit 33. This configuration is beneficial when the volume of gas that must be supplied to cool the probe assembly 10 is so great as to be detrimental to the stability of the interface, or to cool the liquid to solidification, or otherwise harm the measurement if it were to enter the liquid at the forward end 8. In order to control the amount of gas that flows out of the exit 33 through the port 27 and conduit 31, a valve 35 or other flow control device is placed on the conduit 31. The conduit 31 need not be located on the side of the housing 4, but can be located at any position from where it can perform its function.

Figure 10:
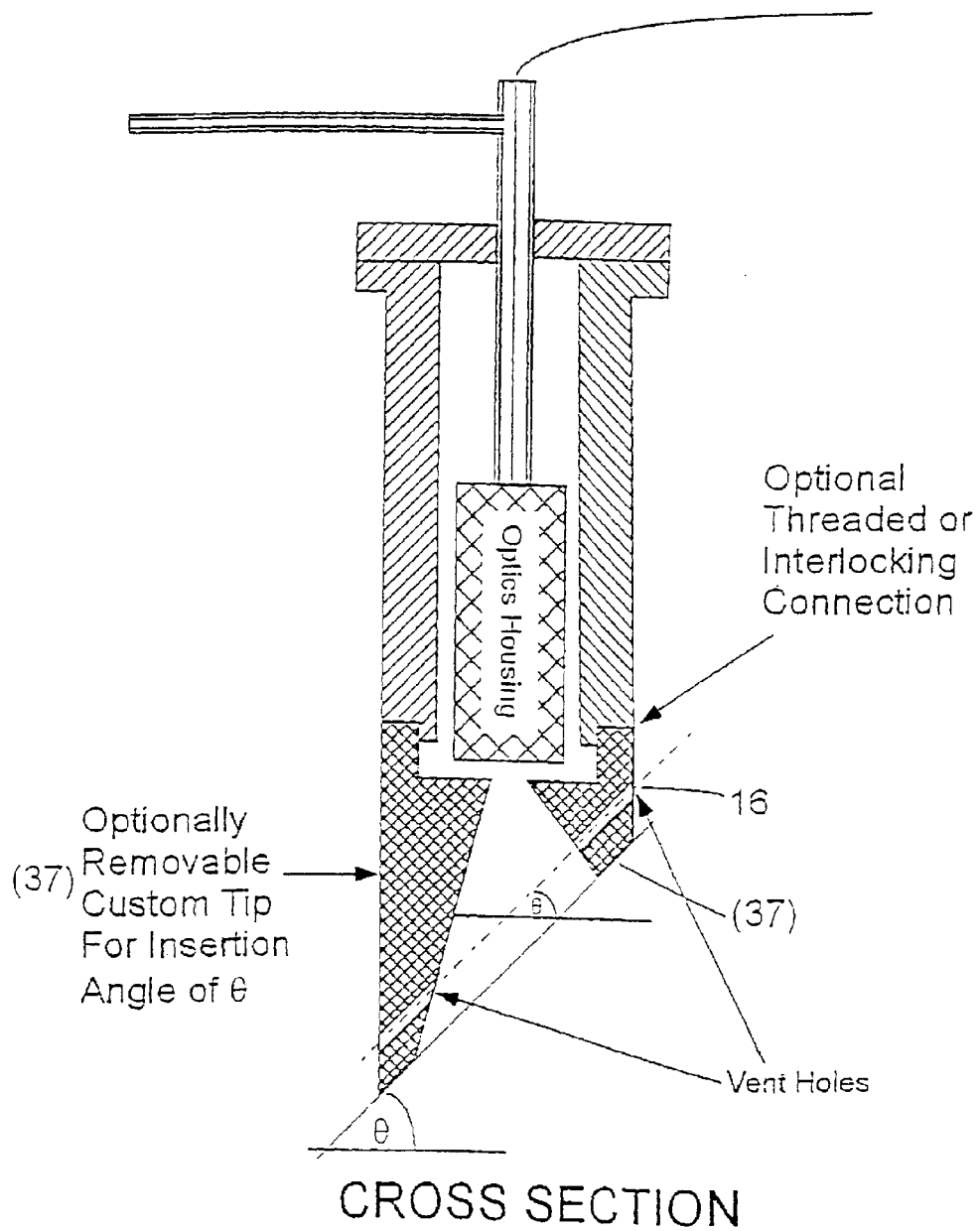
FIG. 10 is a cross-sectional view of another embodiment of the apparatus of the present invention employing a forward end which is angled to facilitate inserting the probe assembly at an angle with respect to the longitudinal axis of the vessel.

The probe assembly does not need to be inserted vertically into the liquid as shown in FIG. 3. In order to facilitate accommodating the probe assembly in many different situations, the forward end 8 of the probe assembly 10 can be configured to be inserted at an angle with respect to the surface of the liquid as shown in FIG. 10. For example, the present invention enables the probe assembly to be inserted through ports positioned in a side wall of a vessel. For example, if the probe assembly were inserted into a wall of a furnace at a 45 degree angle, the bottom surface would be machined at 45 degrees relative to the longitudinal axis of the body of the probe assembly so as to be horizontal thereto or provided with a removable tip 37 having a bottom end machined at an angle $\Theta$ corresponding to the angle of insertion. By matching the angle of insertion to the angle of the forward end 8 of the probe, the liquid surface will be parallel to the face of the forward end 8. This embodiment will keep the liquid out of the probe assembly. By keeping the channels 16 for delivering the inert gas into the liquid parallel to the face of the forward end 8, the channels will always be elevated with respect to the most forward end. As disclosed above, the elevated position of the channels 16 enables the creation of the stable volume of inert gas at the forward end 8.

Figure 19:
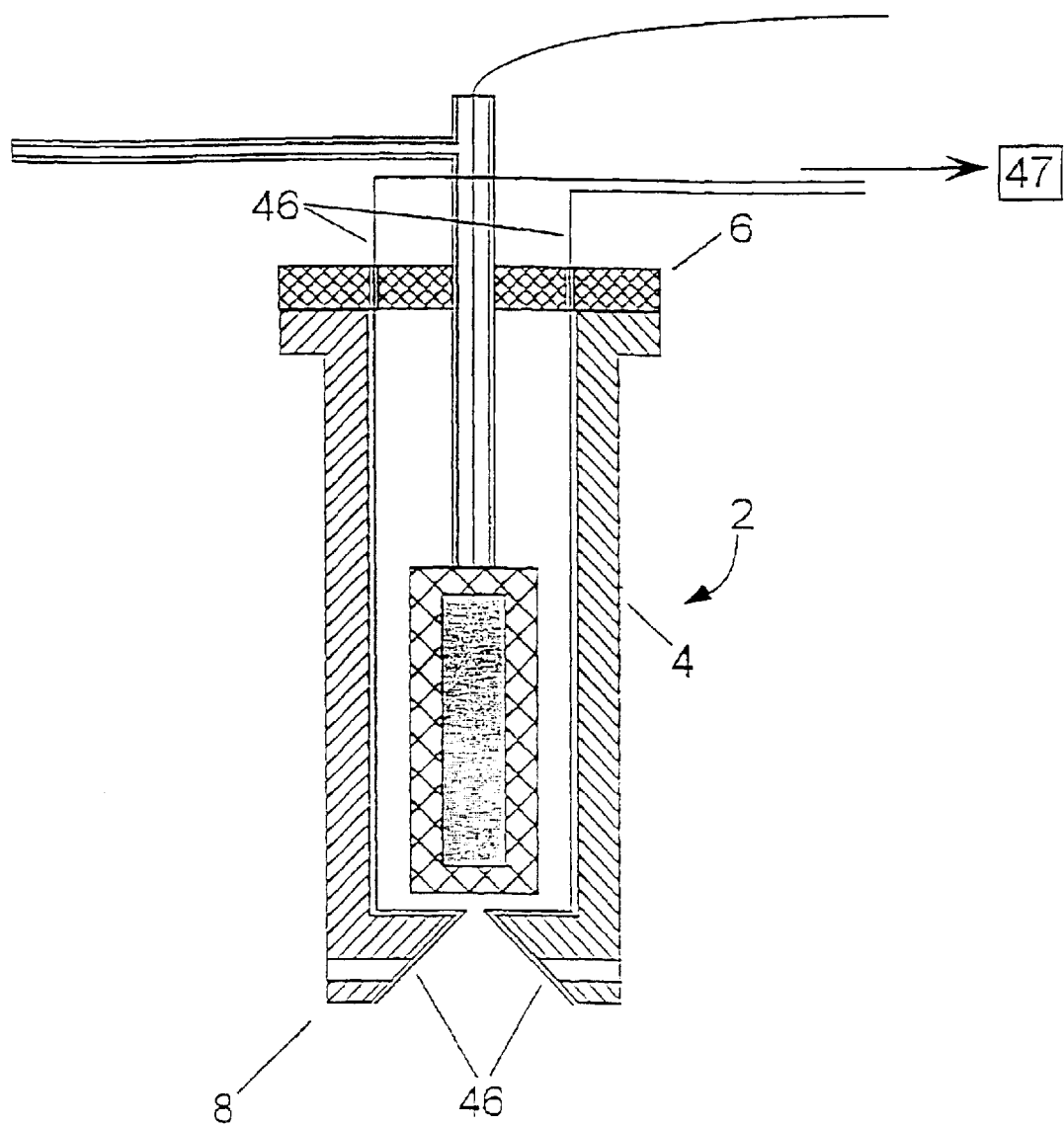
FIG. 19 is a cross-sectional view of another embodiment of the apparatus of the present invention providing an assembly to detect the level of liquid in the forward end of the apparatus.

In certain applications it may be necessary to know the precise location of the liquid-gas interface. In this instance it is advantageous to incorporate an interface detection assembly which can precisely determine the surface of the liquid. One embodiment of an interface detection assembly, if the liquid is electrically conductive, utilizes an electrical circuit comprised of electrical wires with bare ends positioned close to the bottom edge of the probe assembly. When the gas-liquid interface rises to the bare ends, an electrical circuit is completed between the two wires, which activates a signal for the operator or system to take appropriate action such as described below. FIG. 19 illustrates an example of an embodiment of the invention in which the wires 46 are lowered through the rearward end 6 of the probe assembly 2 until the tips reach the forward end 8. The wires 46 may be connected to a sensing apparatus 47. The operator can then finely tune the gas pressure, such as through the use of an automatic controller, so that the least pressure necessary is used to maintain the electrical circuit. In this way, the operator can insure the precise location of the gas-liquid interface created by the electrical circuit comprising the wires 46 and the conductive liquid. Similar methods known to those skilled in the art can be used if the operator requires a minimum or maximum distance of the interface from the tip of the probe assembly.

Interface detection assemblies are particularly useful when the bubbling action of the gas exiting from side openings 19 disturbs the gas-liquid interface causing it to fluctuate. Whether or not this will occur will depend on factors such as the gas pressure and velocity, and the characteristics of the liquid such as density and viscosity. In this case, the operator can vary the method of data collection depending upon the property or properties of the liquid and/or the circumstances under which the measurement is taken, for example, practical limitations on the time available for performing the measurements. For example, the operator may choose to use the completion of the circuit to trigger a measurement event, or, the operator may choose to take a continuous set of measurements, and at a later time correlate the measurements with the time history of the interface, as measured by the mechanism described above, to gain knowledge as to when the interface was in a suitable position for the measurement.

While some inert gas may enter the liquid and escape as bubbles, the stability of the volume of the inert gas is maintained as new inert gas enters through the conduit 18 by allowing the inert gas to escape through the channels 16 via the side openings 19. Thus, by controlling the pressure of the inert gas through the conduit 18 a stable volume of inert gas can be maintained at the interface under a continuous flow of new inert gas. The stable volume of inert gas is temperature controlled by the constant influx of new gas and is thereby prevented from reaching excessive temperatures such as may be obtained when the liquid is a molten metal. By placing one or more temperature sensors (e.g. thermocouples) inside the probe assembly, the temperature of the gas can be monitored. By way of example and referring to FIG. 2 where the temperature sensor 42 is lowered through the rearward end 6 of the probe assembly 2. In this example, the temperature sensor is connected to an exterior temperature measuring device 43, well known to those skilled in the art by electrical wires 44. Output from temperature sensors can be used by the pressure regulator controlling the flow of inert gas to determine if the gas pressure must be increased to maintain suitable temperatures inside the probe.

The term "inert gas" as used herein refers to any gas which does not adversely affect the apparatus and method of the present invention in producing a detectable species from a liquid and in analyzing at least one property of the liquid which may be obtained from the detectable species. Examples of such inert gases will typically include nitrogen, argon, and helium. The inert gases are not limited to those gases which are identified as inert gases but is broader and can include gases which may be reactive in an environment other than in the use intended herein. Also, in certain applications, a reacting gas could be used. In such an application the reacting gas would provide some benefit to the process being measured and would double as either a cooling gas for the probe, an aerodynamic window or both.

The operation of the embodiment of the present invention shown and described in connection with FIGS. 2–4C is shown in FIG. 3. Referring to FIG. 3, there is provided a vessel 30 such as a ceramic crucible containing the liquid in stationary form to be analyzed. The probe assembly 2, having a conduit 18 for the flow of an inert gas includes a housing 4 having a radiation beam assembly therein generally shown by the numeral 10 (FIG. 2) and enclosed in a housing 4 such as a silicon carbide tube. The vessel contains a liquid 20 (e.g. molten metal or glass) and the probe assembly 2 is inserted below the surface thereof. Pressure generated by the flowing inert gas produces a stable volume of inert gas 34 at the interface of the probe assembly 2 and the liquid 20. The pressure of the stable volume of inert gas is preferably maintained by continuously flowing inert gas through the conduit 18 while allowing excess inert gas to escape through the channels 16 via the openings 17 and 19 respectively (See FIGS. 4A–4C) within the nozzle assembly 12. The beam of radiation (e.g. a laser beam) is transmitted into the probe assembly via a fiber optic cable 11 in a known manner and is focused by lenses contained within a lens housing 21 through the stable volume of inert gas 34 present at the interface with the liquid 20.

Figure 5:
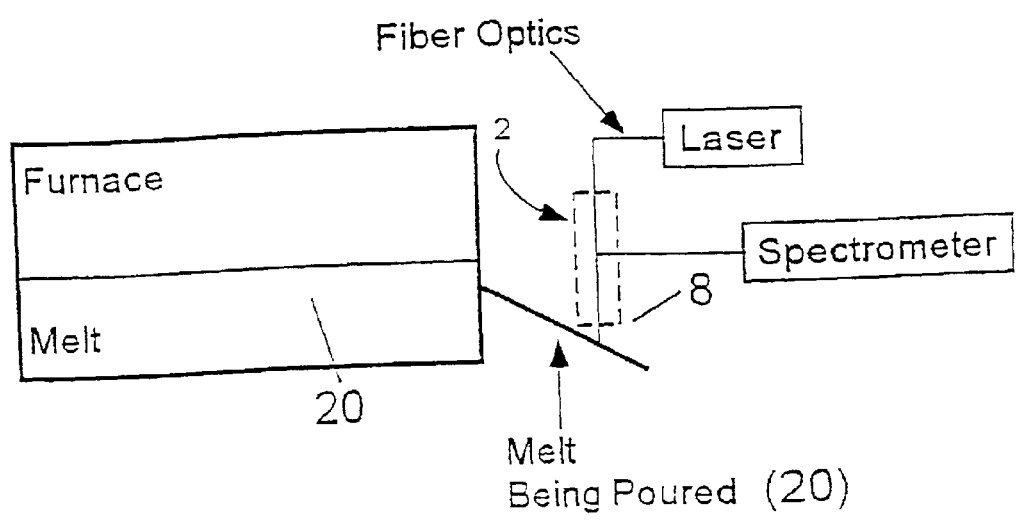
FIG. 5 is a diagrammatic view of an embodiment of the apparatus of the present invention employed to take measurements of a flowing sample of liquid from the surface thereof.

While the present invention has been described to detect properties of liquids in a stationary condition the present invention as shown in FIG. 5, may be used to detect at least one property of a liquid in a flowable condition. The probe assembly 2 shown diagrammatically in FIG. 5 can be submerged to take measurements from the interior of stationary or flowing liquids and can take measurements of the surface of stationary or flowing liquids 20 by placing the tip of the probe assembly above the surface of the flowing liquid. This is particularly advantageous in the production of metals, which are poured from furnaces into molds of different shapes. In this embodiment, the radiation beam is focused upon the upper surface of the liquid to generate detectable species as opposed to the interior of the liquid.

The liquid being analyzed in accordance with the present invention need not be confined to a tank or conduit. The present invention can also be used with stationary or flowing liquids in natural bodies of water such as oceans, lakes, and rivers, regardless of size or of whether the body of water came into existence naturally or is of artificial origin, such as a lake behind a dam.

Figure 11:
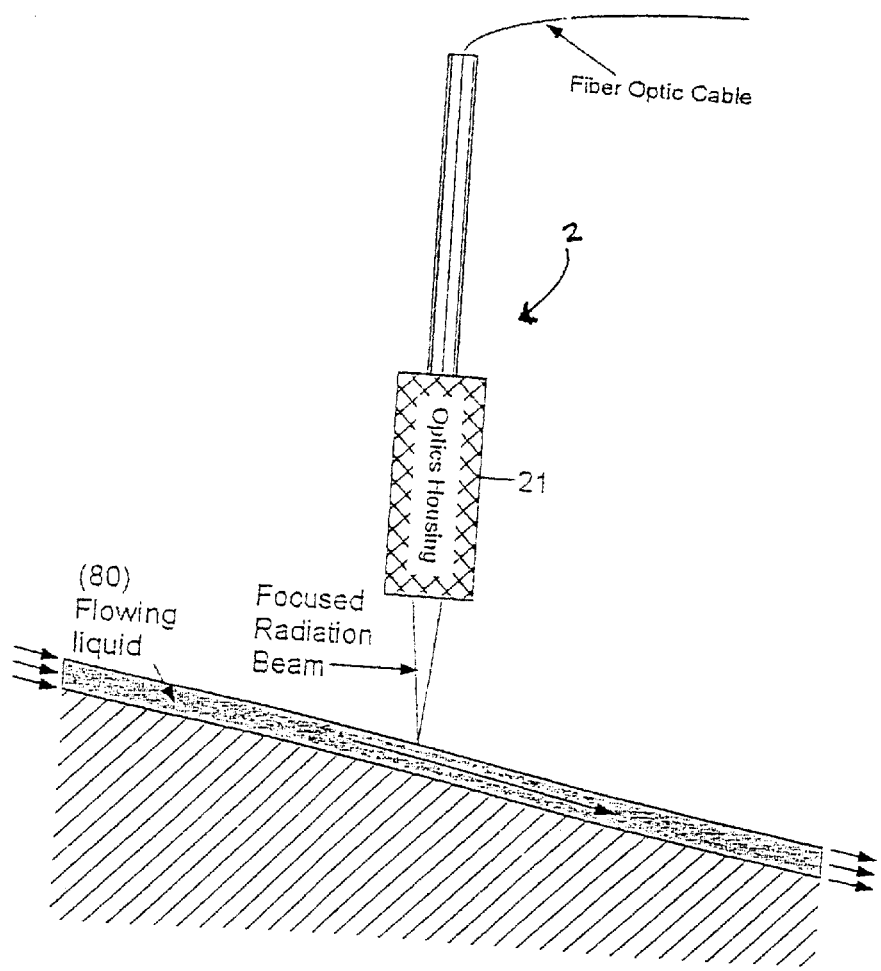
FIG. 11 is a diagrammatic view of another embodiment of the apparatus of the present invention employed when the apparatus is used to analyze flowing liquids from above the surface of the flowing liquid.

If the probe assembly 2 will only be used to analyze the surface of a liquid, stationary or flowing, the probe assembly 2 housing the radiation beam assembly may be fixedly suspended above the liquid as shown in FIG. 11, typically from about a few inches to several feet above the liquid. As shown specifically in FIG. 11, this arrangement is particularly suited for analyzing a flowing liquid represented by the numeral 80. It will be understood that the distance between the radiation beam assembly and the liquid will be selected to generate a detectable species and may be routinely determined by those skilled in the art.

Figure 6:
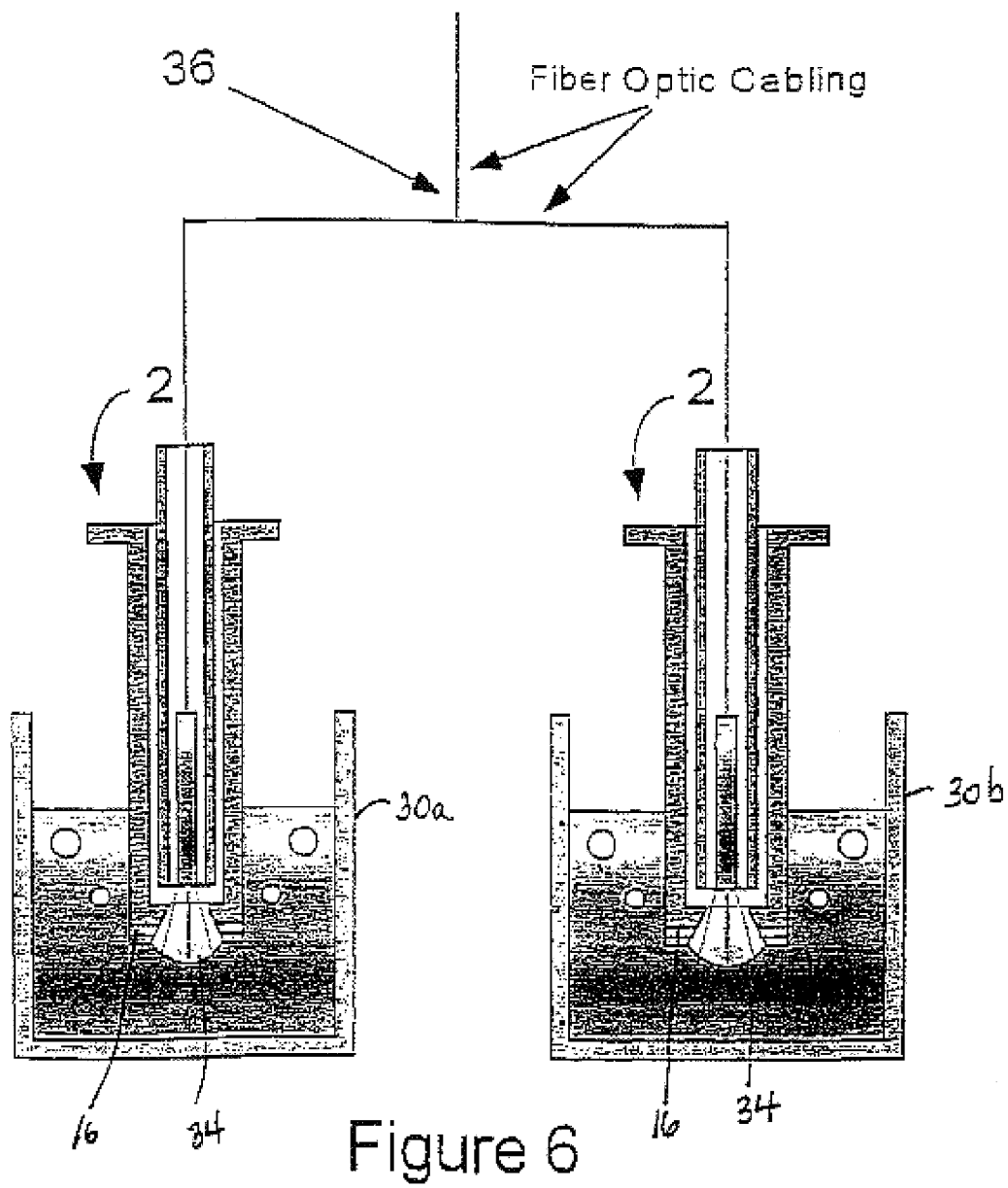
FIG. 6 is a cross-sectional view of another embodiment of the apparatus of the present invention employing multiple probe assemblies for analyzing a liquid contained within multiple vessels.

The present invention encompasses the employment of multiple probe assemblies for measuring multiple locations within a liquid contained within a single vessel or multiple vessels. As shown in FIG. 6, and for exemplary purposes only, two probe assemblies 2 are shown within two vessels 30a and 30b wherein the probe assemblies submerged at the same levels but at different locations. It will be understood that the probe assemblies can be positioned at different levels of the liquid within a vessel or at least one of the probe assemblies can be positioned at the surface of the liquid. The probe assemblies 2 may be interconnected through a common conduit 36 for relaying information regarding the detectable species back to a fewer number of detection devices, preferably a single detection device such as a common spectrometer suitable for this purpose.

Figure 12:
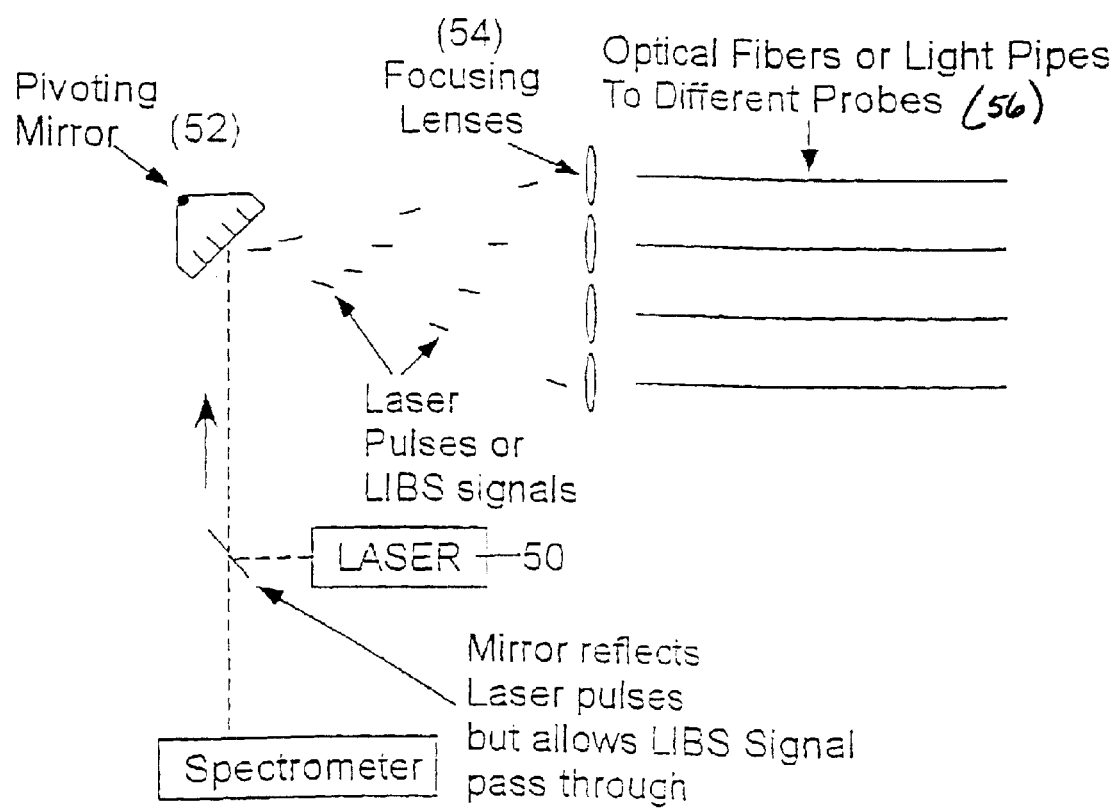
FIG. 12 is a diagrammatic view of another embodiment of the apparatus of the present invention employing multiple probe assemblies, a single radiation source, and a single instrument for measuring a detectable species emanating from the liquid.

The apparatus of the present invention can be employed so that a number of relatively inexpensive probe assemblies can be used simultaneously using a radiation beam assembly and detection device referred to herein as "multiplexing". One embodiment to direct the radiation beam to different probe assemblies while collecting detectable species from each probe assembly is shown in FIG. 12. A radiation beam assembly such as a laser 50 alternately fires into each probe assembly via a pivoting mirror 52, which is synchronized to the laser so that one pulse enters one of a plurality of lenses 54 in conjunction with a like number of probe assemblies (not shown) via respective optical fibers or light pipes shown generally by numeral 56. Since the laser pulses are spaced apart by much more time than is necessary for the detection device (e.g. spectrometer) to read the LIBS signal, there is sufficient time for the mirror to pivot into its correct position for the next pulse. The resulting signal corresponding to the detectable species is thereby alternately received and read by the spectrometer. This allows for multiple measurements from different probe assemblies nearly simultaneously. The readings can be taken from a single furnace (or similar device for containing the liquid) or the probe assemblies can be inserted into several furnaces.

A main advantage of this method is that the probe assemblies are inexpensive as compared to the instrumentation that detects and analyzes the detectable species. By multiplexing several probe assemblies, significant savings can be achieved as compared to using several separate probe assemblies.

The apparatus of the present invention is capable of detecting the identity and concentration of elements (e.g. zinc, nickel, aluminum, etc.) in liquids. When the apparatus is used in conjunction with a laser beam generating assembly the detectable species re-emits optical line radiation, which is gathered by a fiber optic and transmitted to a detection device such as a spectrometer in a conventional manner. This characteristic line radiation is spectrally resolved by the spectrometer which uniquely identifies the elements in the liquid. In addition, the line radiation signal amplitude can be calibrated quantitatively, thus providing the concentration of each element present. All atomic species emit a number of characteristic spectral lines when excited in a plasma.

An advantage of the apparatus of the present invention is that it measures the elemental composition of the liquid in real time and in situ. This provides a continuous reading of the properties of the liquid at any point, which is very valuable to end users of the system. For instance, metal manufacturers can accurately formulate alloys without having to send samples of the molten metal to a laboratory.

Another advantage unique to the present invention is that the expensive and sensitive parts of the apparatus (e.g. spectrometer and laser) are separated from the point of detection and are situated in a safe environment so as not to be damaged, especially when measuring the properties of a molten material.

Figure 7:
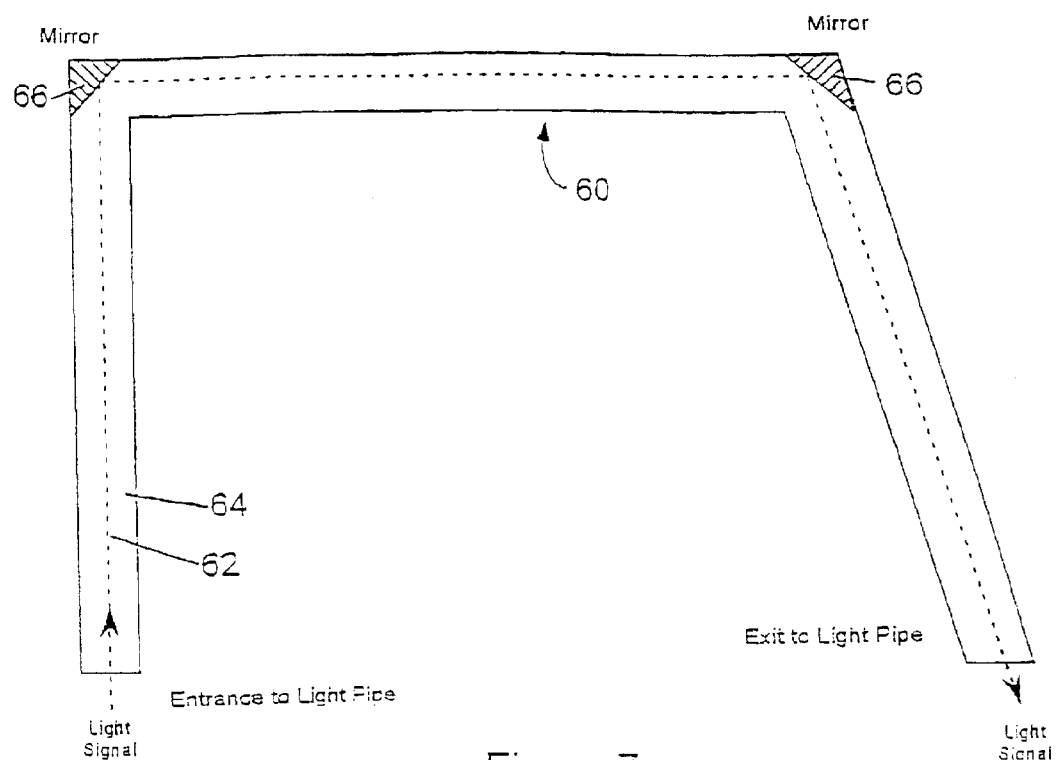
FIG. 7 is a diagrammatic view of a pipe, which can be used to transmit a detectable species such as light energy from the molten material to a device for analyzing the light energy to determine the composition of the molten material.

Although a laser beam generating assembly has been exemplified, any method of transmitting light and the resulting signal (i.e. detectable species) is applicable to the present invention. One example is shown in FIG. 7 employing a light cavity, or light pipe 60, in which the laser beam and light (i.e. detectable species) 62 travel through the probe assembly in a cavity shown generally by the numeral 64. Also, one or more mirrors 66 can be used in the cavity 64 to change the direction of the laser and the light 62 as needed.

This method of transmitting light can be particularly advantageous when transmitting powerful laser pulses over long distances. Fiber optic cables have limitations on the power that they can transmit without damage occurring to the fiber. Inside the light tunnel, or pipe, curved mirrors and/or a combination of mirrors and lenses prevent the light from diverging from its intended path. Another advantage is that light pipes generally cost less than fiber optic cable. The light pipe can be used in combination with fiber optics as well.

Figure 26:
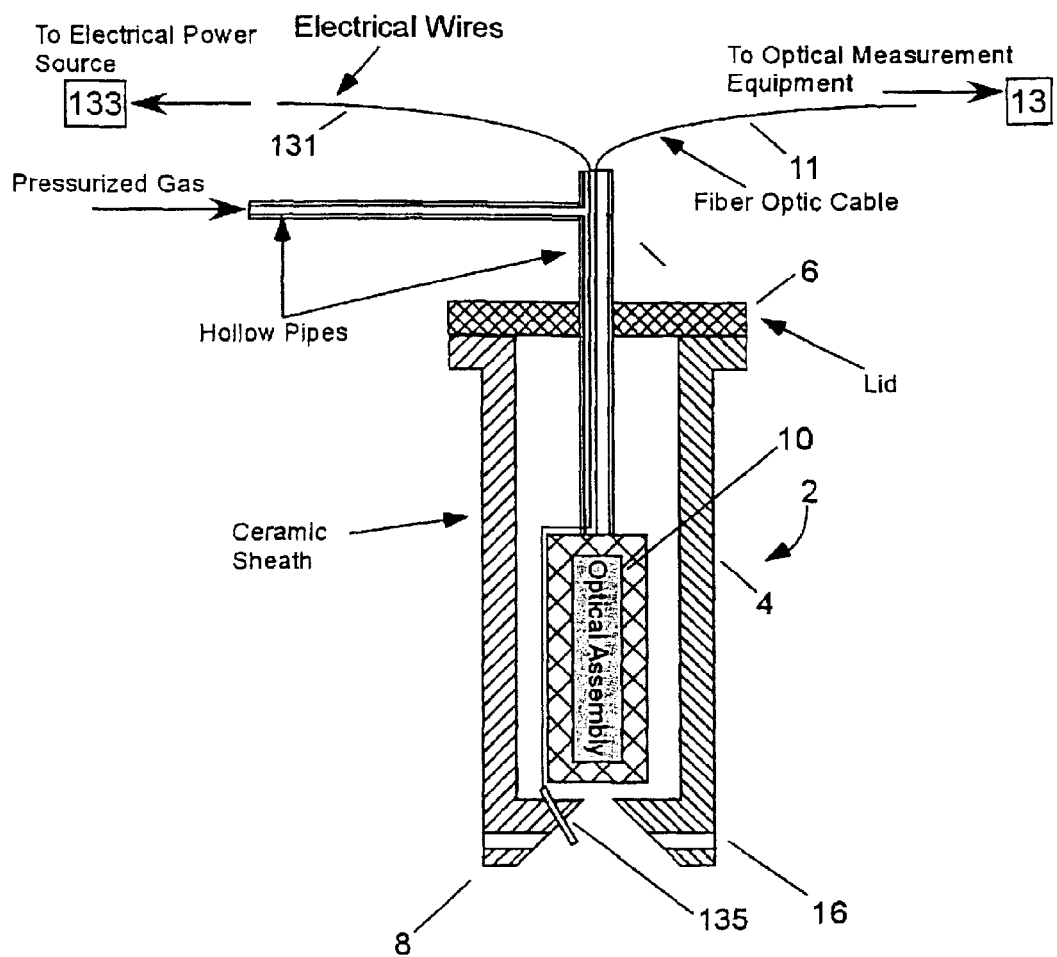
FIG. 26 is a cross-sectional view of a further embodiment of the invention employing an arcing electrode to create a plasma on the gas-liquid interface at the forward end of the probe assembly.

Besides previously referred to laser beam assemblies, the present invention can be used with any device that can create a highly concentrated high energy source. An example of a well known mechanism for measuring at least one property of a liquid utilizes an electrical arc, similar to that in an automotive spark plug, to vaporize and ionize a small amount of a material being analyzed. The light emitted as a result of the spark is at wavelengths characteristic of the material. This process is analogous to the LIBS process, but instead of utilizing laser radiation to excite the liquid, an arc is used. Commercial instruments for this purpose are sold by, for example, Metorex International of Finland and Spectro Analytical Instruments of Germany. The present invention allows for the arc-spark equipment to be brought into close proximity to the interior of the liquid, and for direct optical access to the interior of the liquid. Coolant gas or liquid flowing through the probe assembly, as shown in FIG. 26, provides a temperature controlled environment for the arc-spark equipment. In this embodiment electrical power is forwarded to an electrode 135 via wires 131 from a source 133. In order for the electrode to minimally intrude upon the line of sight of the optics in housing 10, the electrode 135 can be inserted through the forward end of the probe housing 8. A voltage is applied to the electrode at a magnitude sufficient for a spark to jump the gap between the electrode and the liquid. The optical assembly then collects the light generated by the spark and emitted by the plasma via the fiber optic cable to the measurement device 13 that determines the elemental composition of the liquid from the detectable species.

The analytical instrument for making measurements of the properties of the liquid is exemplified herein is a spectrometer such as Acton Research Model 300 and Echelle Model ESA 3000 from LLA. However, any device that can measure the detectable species from the plasma can be used. One such example is a radiometer (e.g. Optoelectronics Model DET 210 Photodetector) that measures the total radiation in a range of wavelengths of light. Such devices can be more cost effective when concentration measurements from a small number of elements are required.

Alternatively, and especially over long distances, a light tunnel can be used comprised of an enclosed box with mirrors at appropriate bends in place of the fiber optic connections in an arrangement which may be similar to the one shown in FIG. 7.

Alternatively, one laser beam assembly can be used for each probe assembly, but all the radiation is collected by one detecting device (e.g. a spectrometer). This configuration is useful when the lasers used are inexpensive, or another inexpensive radiation source is used. Similarly, if radiometers or another inexpensive radiation analyzer is used, it may be practical to multiplex only the laser or other source of radiation, and use one radiation analysis instrument for each probe assembly.

In accordance with the present invention, one fiber cable is shown for transmitting both the laser or other radiation being transmitted into the probe assembly 2, and the detectable species emitted from the liquid and transmitted out of the probe assembly 2 such as shown in FIGS. 2 and 3. This is not intended to be a limitation on the invention, as two or more fiber optic cables or other conduits of the transmitted signal(s) can be used simultaneously. In particular, it can be advantageous to use one optical fiber to transmit the light into the probe assembly 2 and a second optical fiber for relaying the detectable species (e.g. optical signal) out of the probe assembly 2. This is because great care must be taken to avoid damaging an optical fiber when coupling the fiber to a high energy source such as a laser. Further modifying the coupling to allow for separating the light emitted from the probe assembly may complicate the design to an extent where it is impractical due to cost or reliability concerns.

Figure 8:
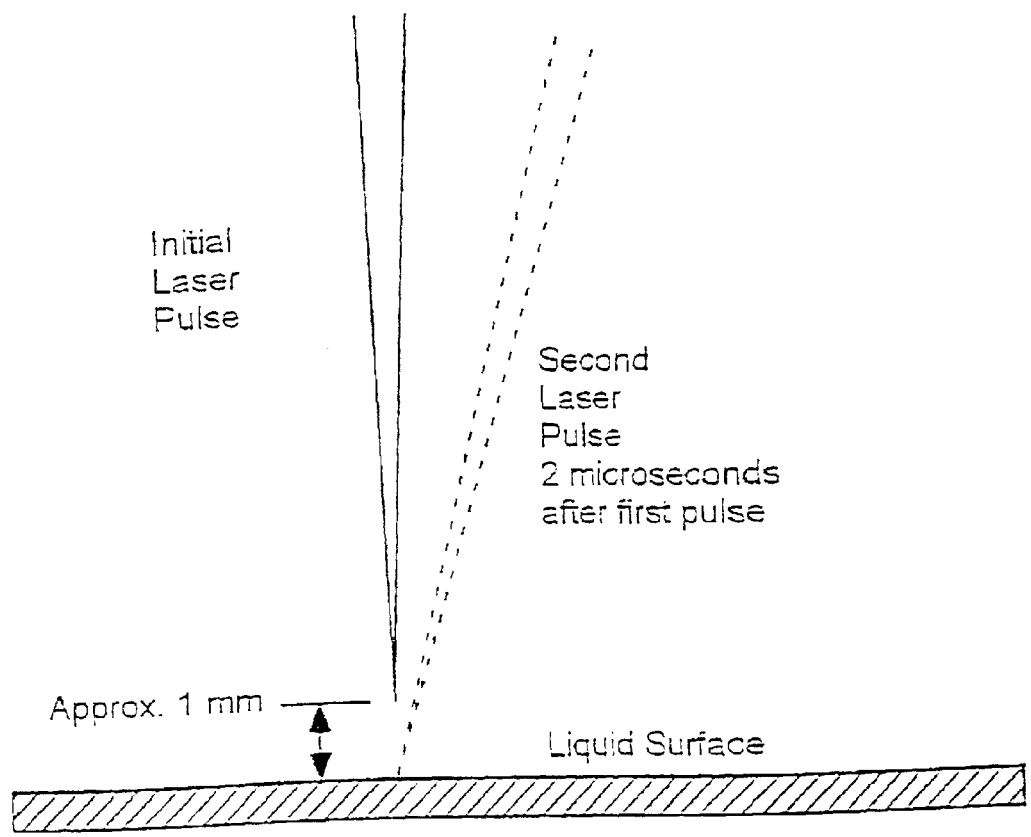
FIG. 8 is a diagrammatic view showing a probe assembly with two lasers to enhance the signal to noise ratio of the LIBS method.

Two or more lasers, or a single laser modified to pulse in quick succession, can be used to enhance the signal to noise ratio. Referring to FIG. 8, a laser is pulsed and focused a set distance above the surface of the liquid such as one mm. A second laser which is focused onto the surface of the liquid is pulsed about 2 microseconds later. The combination of the two pulses provides a very large increase in signal beyond that which can be obtained by a single laser. This method is disclosed in Stratis, D. N., Eland, K. L., and Angel, S. M., "Dual-Pulse LIBS Using a Pre-ablation Spark for Enhanced Ablation and Emission", Applied Spectroscopy, 54, No. 9, 2000, pp. 1270–1274, incorporated herein by reference.

Figure 20:
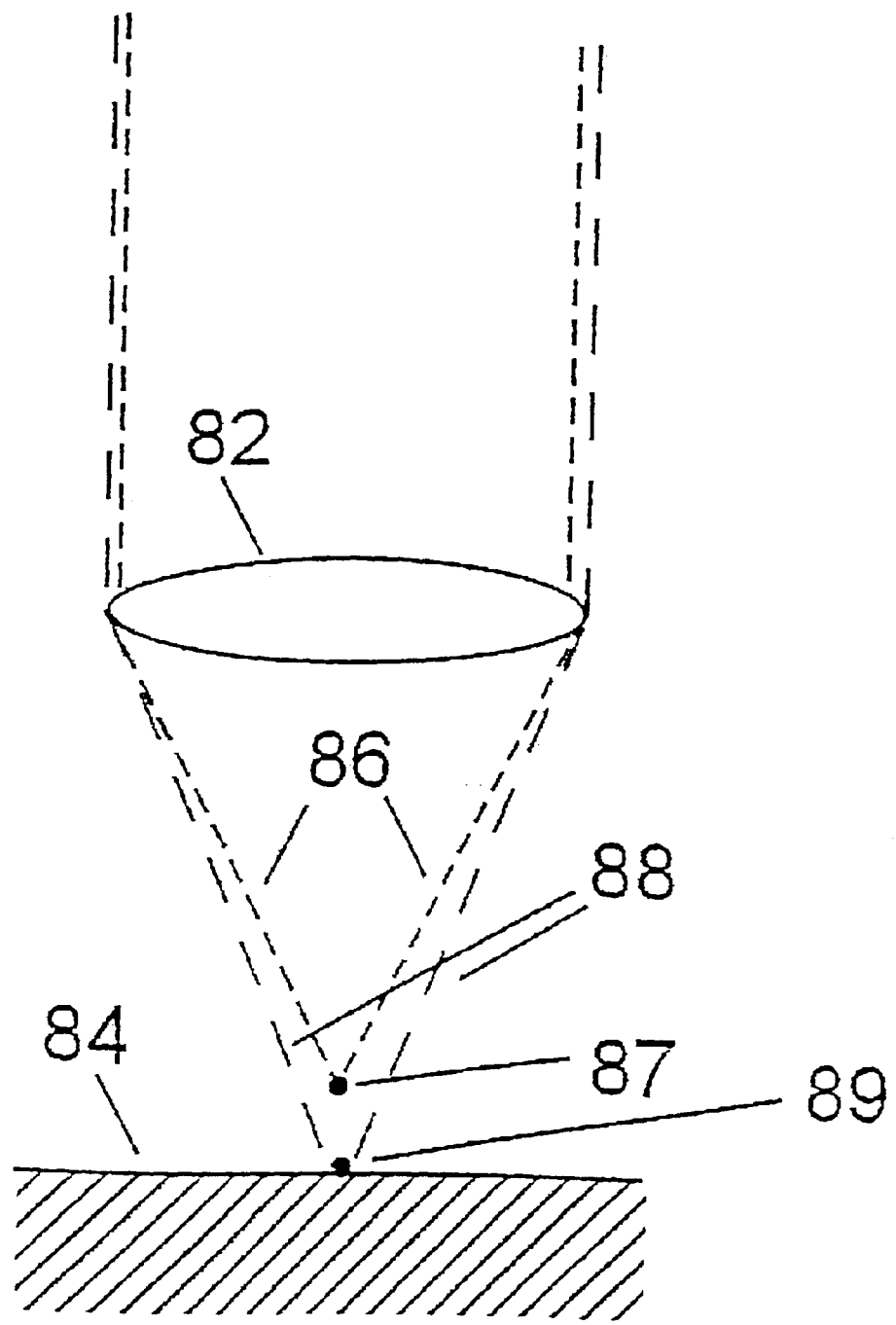
FIG. 20 is a diagrammatical view of a further embodiment of the invention utilizing lasers of two different wavelengths that are collinear to measure the properties of a liquid.

For use with the present invention, the apparatus of Stratis et al. may be modified so that the paths of the laser pulses are co-linear (or nearly so) rather than perpendicular to one another. One such embodiment of this configuration is shown in FIG. 20, which is not meant to be limiting as other configurations are possible. The two lasers described in the Stratis et al. that are used are of different wavelengths. The shorter wavelength beam of light 86 and the longer wavelength beam of light 88 are focused by the lens 82 towards the liquid surface 84. This assembly will generally be inside the housing similar to the lens housing 21 shown in FIG. 3. Generally, materials used for lenses will focus light of shorter wavelengths to short distances as compared to longer wavelengths. This phenomenon is exploited to modify the assembly disclosed in Stratis et al. to be co-linear. In order to initiate the measurement process, a pulse of the shorter wavelength laser light is transmitted first and focused to the point 87 approximately 1 mm above the liquid surface where it generates a spark in the gas above the surface. The second laser pulse of a longer wavelength is transmitted several microseconds later, and if the lens is chosen properly by methods well known to those versed in the art, the longer wavelength light will be focused onto the surface of the liquid 89 creating a LIBS spark on the surface.

Furthermore, the apparatus of Stratis et al. is extended by the present invention to the analysis of liquids and to measuring both the interior and the surface of the liquid, rather than just the surface thereof. Alternatively, one or both of the lasers can be replaced by electrical spark generators such as discussed above.

Figure 21:
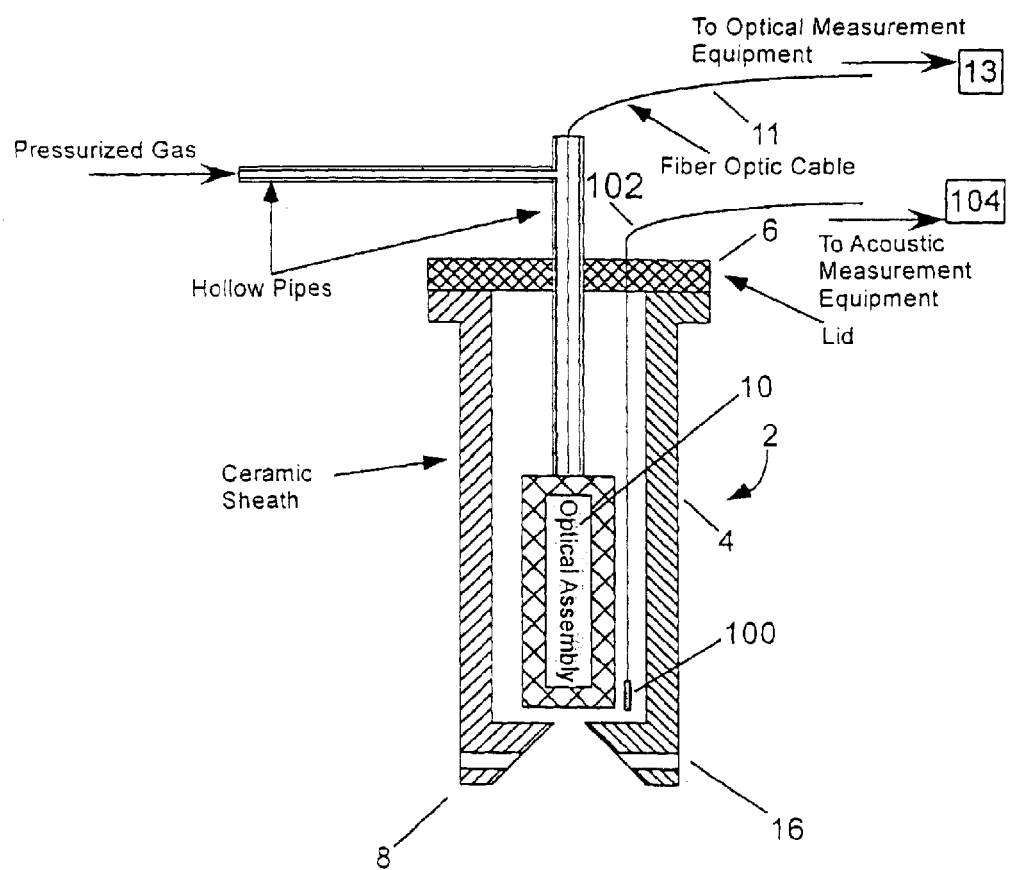
FIG. 21 is a cross-sectional view of a further embodiment of the invention employing an acoustic sensor for detecting a detectable species in the form of acoustic energy emanating from the liquid.

One method of increasing the accuracy of LIBS measurements is to utilize a sensor for measuring the acoustic signal from the LIBS spark. Referring to FIG. 21, an acoustic sensor 100 (e.g. microphone) collects acoustic radiation resulting from the LIBS sparks. This signal is transmitted by wires 102 to acoustic measurement equipment shown generally as 104. Incorporating the magnitude to this acoustic signal into the analysis of the LIBS radiation has been found to increase the accuracy of the measurement of the concentration of the liquid. This method is disclosed in Chaleard, C., Mauchien, P., Uebbing, Andre J., Lacour, L. L., and Geersten, C., "Correction of Matrix Effects in Quantitative Elemental Analysis with Laser Ablation Optical Emission Spectrometry", Journal of Analytical Atomic Spectrometry, Feb. 12, 1997, pp. 183–188, incorporated herein by reference.

Figure 24:
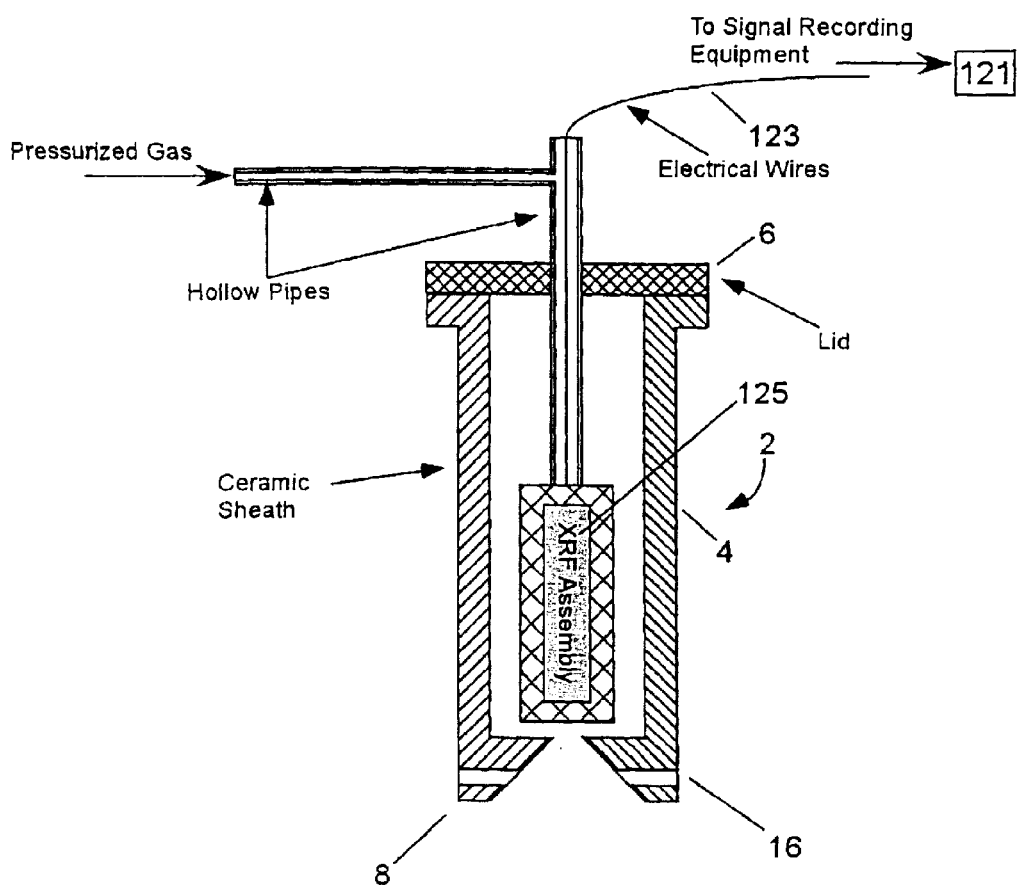
FIG. 24 is a cross-sectional view of a further embodiment of the invention employing an x-ray fluorescence assembly to determine the composition of a liquid.

There are other methods of performing qualitative and quantitative measurements in a liquid that do not rely upon a plasma and are encompassed by the present invention. One such example is known as x-ray fluorescence (XRF) shown in FIGS. 24 and 25. In this method, x-rays are generated by a suitable x-ray beam generating assembly and directed towards the liquid being analyzed. The liquid absorbs the x-rays and emits radiation at wavelengths characteristic of the elemental composition of the liquid. For use in this embodiment of the invention, commercial units are available from, for example, Niton Corporation of Billerica, Mass., and Metorex International of Finland. An assessment of the current product offerings was recently published by Rony E. Ayala Jimenez, "Total Reflection Spectrochmica Acta Part B, 56, 2001, pp. 2331–2336. Currently these units combine the x-ray generation and detection hardware into one compact unit. As shown in FIG. 24, by placing the x-ray beam assembly inside the probe housing, the probe assembly may be brought into close proximity to the interior of the liquid. Referring to FIG. 24, electrical wires 123 provide electrical power from an electrical power source 127 to the XRF assembly 125. Alternatively, electrical power can be provided by one or more batteries located inside the probe assembly 8. The XRF assembly 125 contains well known x-ray generation equipment and directs the x-rays to the forward end of the probe assembly 8. X-rays emitted from the liquid are collected in the XRF assembly and the resulting measurement is transmitted via the electrical wires 123 to a measuring device 121. This electrical signal contains information on the properties of the liquid including elemental composition thereof.

In situations where it is impractical to place the x-ray the assembly equipment inside the probe assembly due to, for example, space limitations, the equipment can be placed outside the probe housing and the x-rays directed down the length of the housing as shown in FIG. 25. The XRF assembly 125 may be placed above a tube 127 through which the x-ray radiation is directed towards the liquid. Niton Corporation, for example, offers an x-ray fluorescence unit with a telescoping nose that incorporates the ability to direct the x-rays in the desired direction.

Figure 13:
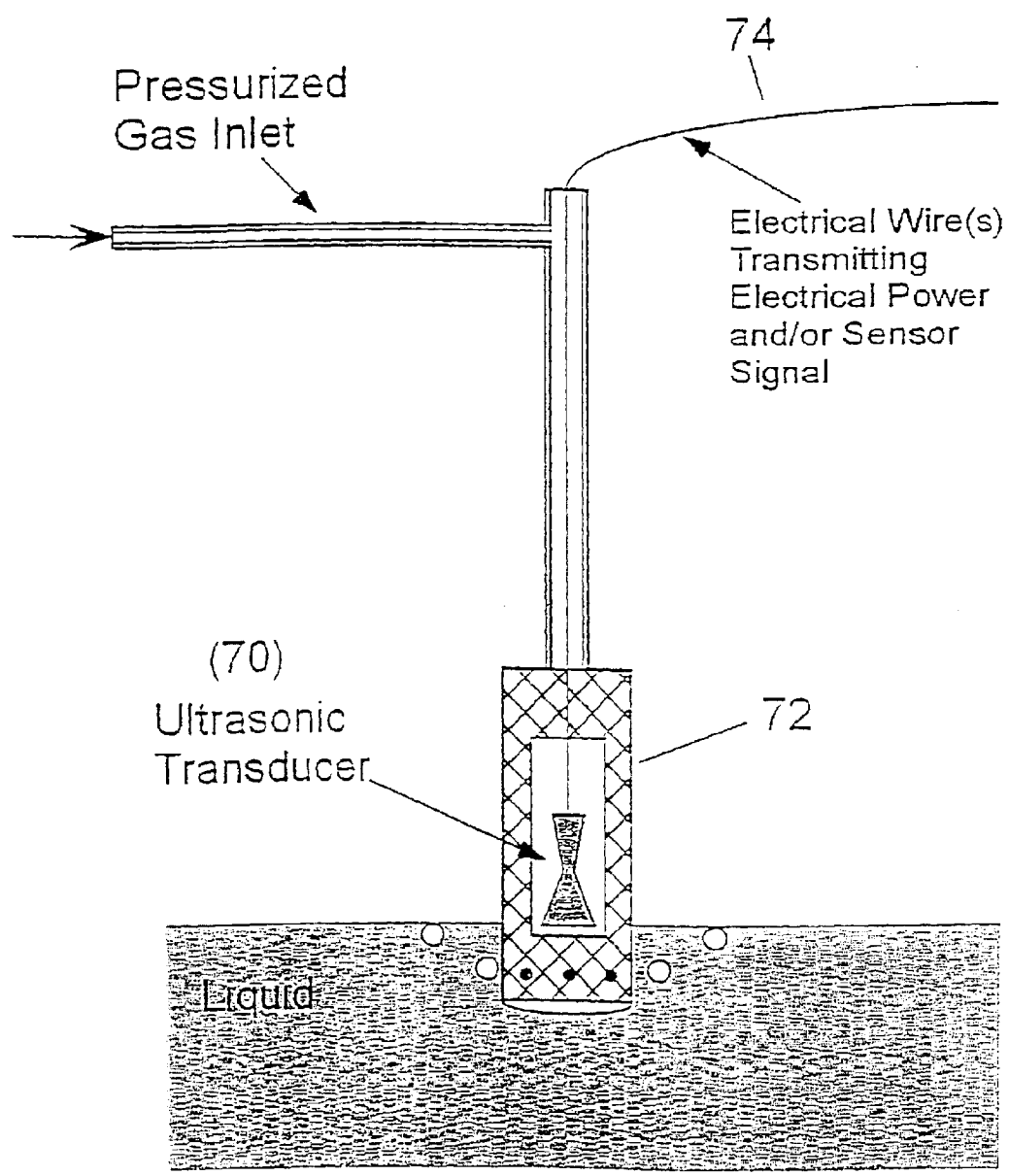
FIG. 13 is diagrammatic view of another embodiment of the apparatus of the present invention employing an ultrasound transducer for performing qualitative and/or quantitative measurements in a liquid.

As shown in FIG. 13, if the detectable species obtained from the liquid is not electromagnetic in nature, as for example obtained by sonic radiation, then the detectable species can be converted via a transducer 70 (e.g. an ultrasonic transducer) inside the probe assembly 72 or immediately outside the probe assembly to an electrical signal. The signal can then be carried away from the probe assembly for analysis via electrical wires 74. This configuration can also be implemented if the detectable species is electromagneic (i.e. light) and the transducer 70 converts electromagnetic signals to electrical signals. Optionally, these electromagnetic signals can be transmitted via radio signals or other wireless communication methods. This would be advantageous when the probe assembly is capable of being self powered via batteries or another on-board energy source.

Figure 27:
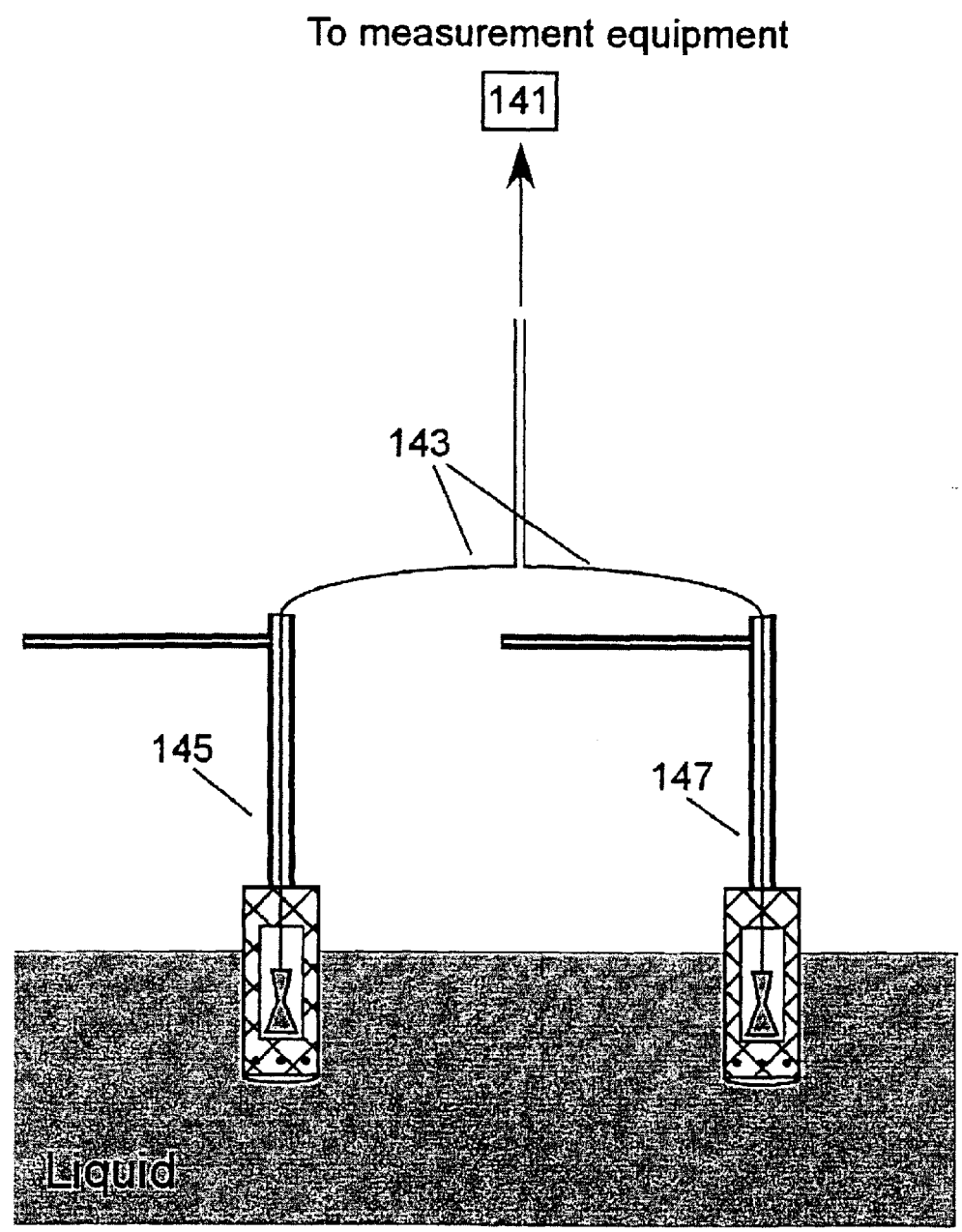
FIG. 27 is a diagrammatical view of a further embodiment of the invention employing two probe assemblies each containing an ultrasonic transducer.

An ultrasonic probe assembly may be utilized to measure, for example, density and flow rates of a liquid. Ultrasonic density probes are commercially available from, for example, Thermo MeasureTech of Austin, Tex. One device such as shown in FIG. 27 uses two probe assemblies spaced a distance apart where one probe assembly emits ultrasonic radiation, and the second probe assembly listens for the radiation. The time required for the ultrasonic waves to travel between the probe assemblies can be correlated to the density of the liquid. This method requires the liquid to be compatible with the probe material. If the liquid is a very hot, such as a molten material, or otherwise incompatible, then the instrument cannot be used. Incorporating the ultrasonic transducer allows for the method to be used in these types of liquids. As disclosed in FIG. 27, two probe assemblies containing ultrasonic transducers are inserted into the liquid. One transducer 145 emits ultrasonic pulses that are received by the other transducer 147. The signals are transmitted to and from measurement devices 141 via wires 143. By knowing the distance between the probe assemblies and other characteristics of the liquid, such as temperature and composition, the fluid density can be calculated by those versed in the art.

Similarly, ultrasonic flowmeters utilize the time required for ultrasonic saves to travel between two probe assemblies to determine the flow rate of the liquid. Instruments based on this principle are commercially available from, for example, Panametrics Inc. of Houston, Tex. As in the case of the density meter, for very hot liquids or liquids that are similarly incompatible with common transducer materials, incorporating the ultrasonic transducer into the present invention allows for the method to be used.

Ultrasonic and XRF methods are examples of methods for measuring properties of liquids that do not rely on creating a plasma, but can be incorporated into the present invention. Because these methods deliver radiation from the liquid, and receive a detectable species therefrom, they can alternatively use, in an embodiment of the invention were a protective barrier (e.g. a window 9) can be used in place of a stable volume of gas, electromagnetic or sonic radiation to generate a detectable species as shown in FIG. 18.

One application of the present invention is directed to the selective in-line alloying during a pour of molten material. In this application, a probe assembly is situated directly on top of the molten material in a trough as it is being poured from a furnace, as shown in FIGS. 5 and 11. It is possible to take measurements of all of the elements of interest and use that data as a feedback to control the feedstock. Alternatively, one or two selected elements can be measured such as magnesium and manganese. These elements can be alloyed in the trough as the flowing molten material 80 is being poured and can be controlled by input from a sensor (not shown; the balance of the alloying would have been previously accomplished in the furnace in a conventional manner). If only one element is being alloyed, then at least one radiometer, typically two can be used to replace the spectrometer.

Figure 14:
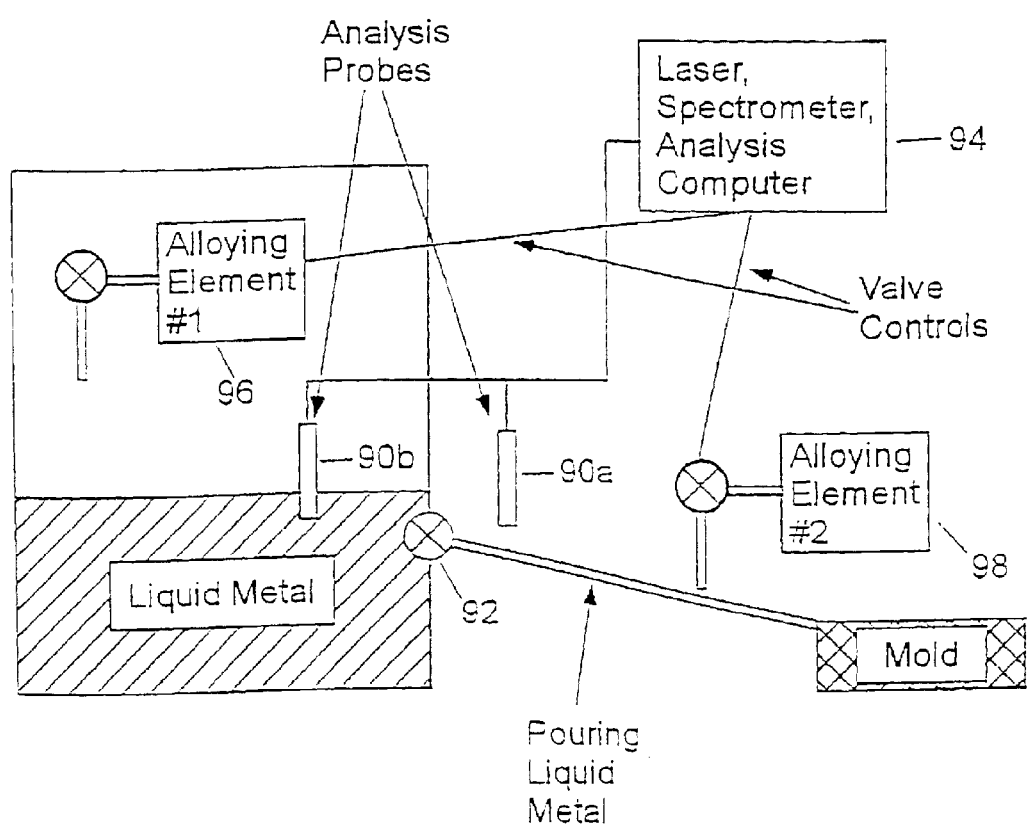
FIG. 14 is a diagrammatic view of an embodiment of the present invention which can be utilized in the production of metal alloys by means of in-line alloying.

It may be advantageous to use two or more probe assemblies to perform in-line alloying as seen in FIG. 14. Two probe assemblies 90a and 90b may share a single laser and spectrometer 94, using the multiplexing technique described above. In this embodiment, one probe assembly 90a analyzes the stream being poured and a second probe assembly 90b is positioned inside the furnace to analyze the pool of liquid. The benefit of this embodiment is that two step alloying can be performed in which one alloying step is performed inside the furnace, and the second step is performed on the pouring liquid. This is useful if one alloying element is added in large quantities as indicated by numeral 96 and one alloying element as indicated by numeral 98 is added in smaller quantities. The alloying element that is added in larger quantities would be mixed into the pool of liquid inside the metal, where it is easier to mix it throughout, and the element added in small quantities is mixed into the stream, where it can mix in easily. Additionally, the probe assembly 90b inside the furnace can be used to trigger a warning in the event of an improperly formulated melt. In a continuous furnace, it can be used to control a valve 92, or any other device capable of stopping the flow of material such as a plug, that stops the continuous stream of molten metal from being poured in the event of an error in the formulation.

Figure 15:
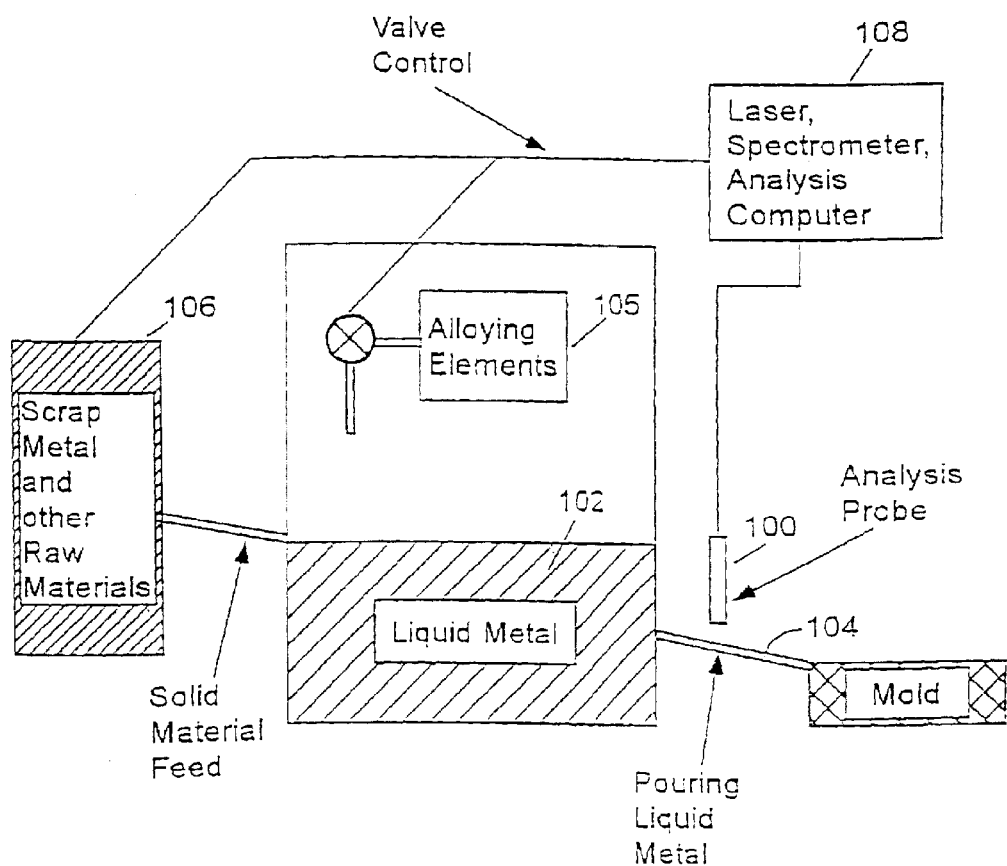
FIG. 15 is a diagrammatic view of an embodiment of the present invention which can be utilized in the production of metal alloys by means of a continuous output furnace.

Another application of the present invention concerns converting a conventional batch furnace into a continuous furnace, as shown in FIG. 15. The implications of this are significant and could result in a new operating paradigm for the aluminum or similar industries. In this application, a probe assembly 100 is again positioned immediately above the molten metal 102 in a trough 104 as the molten metal is being poured. However, all the elements of interest are being read and controlled. The furnace is continuously and simultaneously pouring and charging through a source of metal 106. The furnace alloying takes place in the furnace, also in a continuous manner. As the probe assembly 100 sends detectable species to a detection device (e.g. spectrometer 108) for analysis, records are made of the concentration of one or more of the elements. Thus, the operator may either manually or automatically adjust the scrap metal feed and the alloying elements feed 105 to keep the alloy within specification. One or more probe assemblies can be positioned inside the furnace as well (See FIG. 14) to facilitate the process. The benefits of a continuous furnace are significant and include energy reduction, production increase, and emission reduction.

Figure 16:
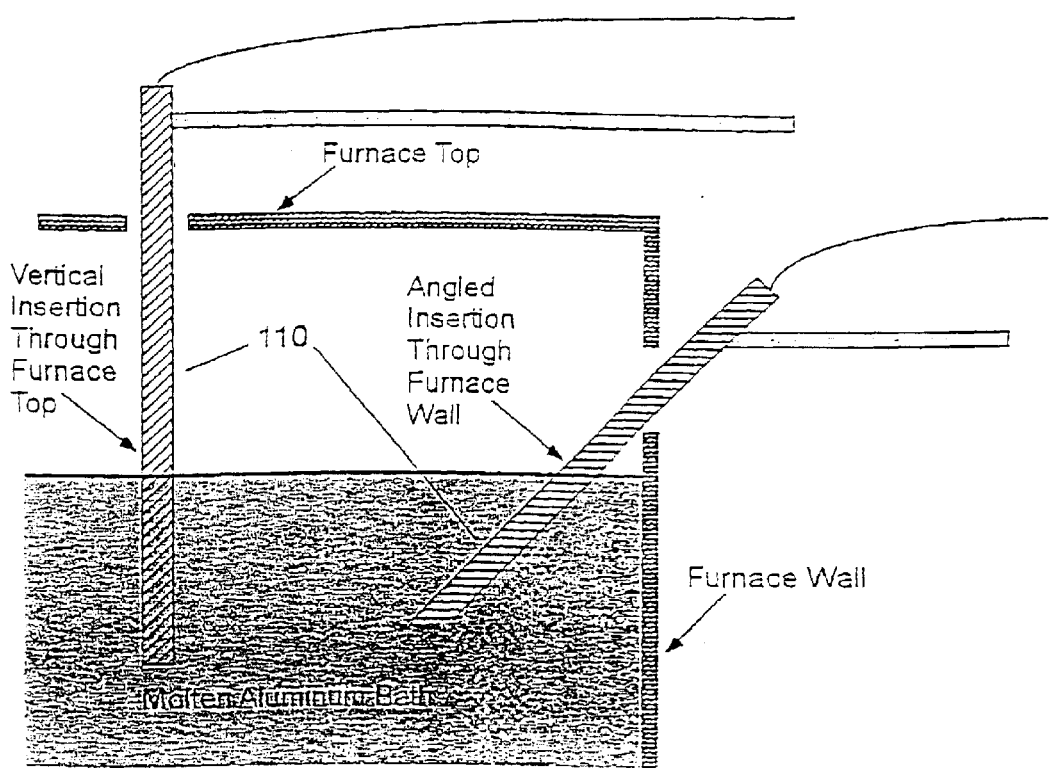
FIG. 16 is a diagrammatic view of an embodiment of the present invention which can be used to simultaneously measure properties of a liquid in multiple locations within a vessel.

Further application of the present invention is its use as a diagnostic tool to measure thermal and mass transfer inside the melt so as to improve furnace modeling (i.e. predictions of furnace performance). Raw materials such as scrap metal or alloying materials would be added to the melt in the ordinary fashion. The probe assembly may be immersed in the molten material at one location, and the change in melt composition as a result of the addition of the new materials may be measured as a function of time. This process, as shown in FIG. 16, may be repeated with the probe assembly 110 in different locations, creating a spatial and temporal map of how the composition of the melt varies when new materials are added. By incorporating temperature measurement into the probe assembly capability see, for example, (FIG. 2, reference numerals 42–44), temperature fluctuations as a result of charging the furnace can be similarly mapped.

Alternatively, the effect of allowing the melt to settle for prolonged periods of time may be measured. Since molten metal used in production is typically comprised of many species, some heavier than others, if a melt is allowed to sit undisturbed, the heavier constituents naturally fall to the bottom, creating a stratified melt as opposed to the desired homogeneous composition. To date, it is not possible to measure the degree of stratification as a function of idle time or location in the furnace. By inserting the probe assembly into different locations at different depths in the furnace, and measuring composition as a function of time, the process of stratification can be studied. The resulting knowledge can then be used to change operating procedures and furnace designs to avoid stratification.

Stratification can also occur due to thermal currents. When a liquid that conducts heat slowly, such as molten glass, is heated, the heat is transported unevenly by thermal currents. These currents can also carry melt constituents, with the result being that constituents are concentrated or depleted from certain areas of the tank.

The information gleaned from these experiments would be used to redesign furnaces and operating procedures to produce homogenous melts with increased efficiency. Towards this end, computer software that is used to simulate furnace operation or other mixing tanks could incorporate the temporal and spatial concentration maps mentioned above to increase their accuracy. Currently, this type of software relies on theoretical calculations alone or in combination with much less performance data than can be collected by the present invention.

What is claimed is:

1. An apparatus for measuring at least one property of a liquid at or below the surface of the liquid comprising:
   a) a housing having a forward end;
   b) at least one probe assembly contained within the housing, said at least one probe assembly comprising means for introducing an inert gas into the housing, a conduit for channeling the inert gas to the forward end of the housing and means for providing a stable volume of the inert gas between an open area of the forward end of the housing and the liquid including pressure control means for automatically maintaining the stable volume of the inert gas at the forward end of the housing at a pressure sufficient to keep the liquid from entering the forward end of the housing and the probe assembly, and means for moving the at least one probe assembly to any depth or angle in said liquid while maintaining the stable volume of inert gas;
   c) a radiation beam assembly comprising means for generating a beam of radiation sufficient to vaporize a portion of the liquid into a detectable species, means for transmitting the radiation beam through the forward end of the housing to the interface of the liquid and the stable volume of inert gas; and
   d) detection means for receiving the detectable species and for detecting from said detectable species at least one property of the liquid.

2. The apparatus of claim 1 wherein the inert gas generating means further comprising means for generating a continuous flow of inert gas to the forward end of the housing.

3. The apparatus of claim 1 wherein the means for generating a beam of radiation is positioned external of the housing.

4. The apparatus of claim 1 wherein the means for generating a beam of radiation is positioned internal of the housing.

5. The apparatus of claim 1 comprising a plurality of probe assemblies.

6. The apparatus of claim 5 wherein at least one probe assembly of the plurality of probe assemblies is directed towards a first portion of the liquid contained within a vessel and at least one other probe assembly is directed towards a second portion of the liquid which is flowing.

7. The apparatus of claim 1 wherein the at least one of the probe assemblies is positioned within the liquid.

8. The apparatus of claim 1 wherein at least one of the probe assemblies is positioned at or above the surface of the liquid.

9. The apparatus of claim 1 wherein the liquid is a molten material.

10. The apparatus of claim 9 wherein the molten material is a molten metal or a molten glass.

11. The apparatus of claim 1 wherein the radiation beam assembly comprises means for forming a beam of radiation comprising at least one wavelength from the electromagnetic spectrum.

12. The apparatus of claim 11 wherein the at least one wavelength is selected from the group consisting of x-ray, ultraviolet, radio, infrared and microwave.

13. The apparatus of claim 1 wherein the beam of radiation is a laser beam.

14. The apparatus of claim 13 comprising a laser induced breakdown spectroscopy system.

15. The apparatus of claim 14 further comprising a sensor for measuring an acoustic signal generated from the laser induced breakdown spectroscopy system.

16. The apparatus of claim 13 comprising a light cavity for transmitting the laser beam to the liquid and the detectable species from the liquid to the detection means.

17. The apparatus of claim 1 wherein the beam of radiation is a sonic beam.

18. The apparatus of claim 1 wherein the detection means is a spectrometer.

19. The apparatus of claim 1 wherein the detection means is radiometer.

20. The apparatus of claim 1 wherein the forward end of the housing comprises a nozzle assembly comprising at least one first opening for enabling the inert gas to contact the liquid and the pressure control means.

21. The apparatus of claim 20 wherein the pressure control means comprises at least one channel for delivering the inert gas away from the interface of the housing and the liquid.

22. The apparatus of claim 21 wherein the channel comprises a first opening for receiving the inert gas and a second opening above the at least one first opening when the apparatus is operatively positioned to determine said property.

23. The apparatus of claim 22 wherein the second opening is below the surface of the liquid.

24. The apparatus of claim 22 wherein the second opening is above the surface of the liquid.

25. The apparatus of claim 20 further comprising temperature control means for controlling the temperature within the apparatus.

26. The apparatus of claim 25 wherein the temperature control means comprises a second stream of gas or liquid in proximity but not in contact with the stable volume of inert gas.

27. The apparatus of claim 1 further comprising excess gas evacuation means for removing excess gas from the gas used to form the stable volume of inert gas.

28. The apparatus of claim 1 comprising a plurality of conduits for delivering a plurality of inert gas streams to the forward end of the housing to form and maintain the stable volume of the inert gas.

29. The apparatus of claim 1 wherein the liquid is contained within a vessel having a longitudinal axis, the forward end of the housing being constructed at an angle $\Theta$ with respect to the longitudinal axis of the vessel to enable the probe assembly to be inserted into a side wall of the vessel.

30. The apparatus of claim 29 wherein the angle $\Theta$ is about 45°.

31. The apparatus of claim 1 further comprising an interface detection assembly for detecting the surface of the liquid at the an interface of the liquid and the stable volume of inert gas.

32. The apparatus of claim 31 wherein the interface detection assembly comprises an electrical circuit means at the forward end of the housing that forms an electrical circuit when the electrical circuit means contacts the surface of the liquid.

33. The apparatus of claim 32 wherein the liquid is an electrically conductive liquid.

34. The apparatus of claim 1 wherein the liquid is flowing.

35. The apparatus of claim 34 wherein the at least one probe assembly is positioned above the surface of the flowing liquid.

36. The apparatus of claim 1 for measuring at least one property of the liquid at the surface of the liquid, wherein the at least one probe assembly is fixedly suspended above the liquid.

37. The apparatus of claim 1 comprising a plurality of probe assemblies.

38. The apparatus of claim 37 wherein the plurality of probe assemblies are positioned at different locations within a vessel containing the liquid.

39. The apparatus of claim 37 wherein the plurality of probe assemblies are positioned at different depths within the vessel.

40. The apparatus of claim 37 wherein the plurality of probe assemblies are operatively connected to a fewer number of radiation beam assemblies.

41. The apparatus of claim 37 wherein the plurality of probe assemblies are connected to a single radiation beam assembly.

42. The apparatus of claim 37 wherein the plurality of probe assemblies are connected to fewer number of detection means.

43. The apparatus of claim 37 wherein the plurality of probe assemblies are connected to a single detection means.

44. The apparatus of claim 1 wherein the radiation beam assembly comprises an electric arc generator.

45. The apparatus of claim 44 comprising an electrode spaced apart from the liquid and electrically connected to the electric arc generator, wherein said electric arc generator generates sufficient electrical power to cause an arc to pass from the electrode to the liquid to thereby generate the detectable species from the liquid.

46. The apparatus of claim 1 wherein the radiation beam assembly comprises means for delivering a plurality of radiation pulses to the stable interface in a manner which enhances the signal to noise ratio.

47. The apparatus of claim 46 wherein the radiation beam pulses are collinear or are about collinear.

48. The apparatus of claim 1 wherein the radiation beam assembly comprises an ultrasonic radiation assembly, wherein the properties of the liquid that are measured include density and flow rate.

49. The apparatus of claim 1 further comprising a protective barrier between the radiation beam assembly and the liquid, said protective barrier enabling the radiation beam to pass therethrough to generate the detectable species.

50. A method of measuring at least one property of a liquid at or below the surface of the liquid comprising:
1) placing at least one apparatus into the liquid, said apparatus comprising:
a) a housing having a forward end;
b) at least one probe assembly contained within the housing, said at least one probe assembly comprising means for introducing an inert gas into the housing, a conduit for channeling the inert gas to the forward end of the housing and means for providing a stable volume of the inert gas between an open area of the forward end of the housing and the liquid including pressure control means for automatically maintaining the stable volume of inert gas at a pressure sufficient to keep the liquid from entering the probe assembly, and means for moving the probe assembly to any depth or angle in said liquid while maintaining the stable volume of inert gas;
c) a radiation beam assembly comprising means for generating a beam of radiation sufficient to vaporize a portion of the liquid into a detectable species, means for transmitting the radiation beam through the forward end of the housing to the interface of the liquid and the stable volume of inert gas; and
d) detection means for receiving the detectable species and for detecting from said detectable species at least one property of the liquid, into the liquid; and 2) measuring the at least one property of the liquid from the detectable species.

51. An apparatus for measuring at least one property of a liquid at or below the surface of the liquid comprising:
a) a housing having a forward end;
b) at least one probe assembly at the forward end of the housing, said probe assembly comprising an inert gas generating means comprising a source of inert gas, a conduit for channeling the inert gas to the forward end of the housing and a nozzle assembly comprising at least one first opening for enabling the inert gas to contact the liquid and form a stable volume of inert gas at the interface of the forward end of the housing and the liquid and pressure control means for maintaining the inert gas in contact with the liquid at said stable volume;
c) a radiation beam assembly comprising means for generating a beam of radiation sufficient to vaporize a portion of the liquid into a detectable species, means for transmitting the radiation beam through the forward end of the housing to the interface of the liquid and the stable volume of inert gas; and
d) detection means for receiving the detectable species and for detecting from said detectable species at least one property of the liquid.

52. The apparatus of claim 51 wherein the pressure control means comprises at least one channel for delivering the inert gas away from the interface of the housing and the liquid.

53. The apparatus of claim 52 wherein the channel comprises a first opening for receiving the inert gas and a second opening above the at least one first opening when the apparatus is operatively positioned to determine said property.

54. The apparatus of claim 53 wherein the second opening is below the surface of the liquid.

55. The apparatus of claim 53 wherein the second opening is above the surface of the liquid.

56. The apparatus of claim 51 further comprising temperature control means for controlling the temperature within the apparatus.

57. The apparatus of claim 56 wherein the temperature control means comprises a second stream of gas or liquid in proximity but not in contact with the stable volume of inert gas.

58. The apparatus of claim 51 wherein the liquid is contained within a vessel having a longitudinal axis, the forward end of the housing being constructed at an angle Θ with respect to the longitudinal axis of the vessel to enable the probe assembly to be inserted into a side wall of the vessel.

59. The apparatus of claim 58 wherein the angle Θ is about 45°.

60. The apparatus of claim 51 comprising a plurality of probe assemblies positioned at different depths within the vessel with each probe assembly operatively connected to a single radiation beam assembly.

61. The apparatus of claim 51 comprising a plurality of probe assemblies wherein the plurality of probe assemblies are operatively connected to a fewer number of radiation beam assemblies.

62. The apparatus of claim 51 comprising a plurality of probe assemblies wherein the plurality of probe assemblies are connected to fewer number of detection means.

63. The apparatus of claim 51 wherein the plurality of probe assemblies are connected to a single detection means.

64. The apparatus of claim 51 wherein the plurality of probe assemblies are connected to a single radiation beam assembly.

65. A method of measuring at least one property of a liquid at or below the surface of the liquid comprising:

1) positioning an apparatus in proximity to the liquid, said apparatus comprising:
   a) a housing having a forward end;
   b) at least one probe assembly contained within the housing, said at least one probe assembly comprising means for introducing an inert gas into the housing, a conduit for channeling the inert gas to the forward end of the housing and means for providing a stable volume of the inert gas between an open area of the forward end of the housing and the liquid including pressure control means for automatically maintaining the stable volume of the inert gas at the forward end of the housing at a pressure sufficient to keep the liquid from entering the forward end of the housing and the probe assembly, and means for moving the at least one probe assembly to any depth or angle in said liquid while maintaining the stable volume of inert gas;
   c) a radiation beam assembly comprising means for generating a beam of radiation sufficient to vaporize a portion of the liquid into a detectable species, means for transmitting the radiation beam through the forward end of the housing to an interface of the liquid and the stable volume of inert gas; and
   d) detection means for receiving the detectable species and for detecting from said detectable species at least one property of the liquid, 2) generating a radiation beam sufficient to vaporize a portion of the liquid into a detectable species;

3) transmitting the radiation beam through the forward end of the housing to an interface of the liquid and the stable volume of inert gas, and 4) detecting at least one property of the liquid from the detectable species.

66. The method of claim 65 wherein the method is conducted within a batch furnace or a continuous furnace.

67. The method of claim 66 wherein the method is conducted in a batch furnace.

68. The method of claim 66 wherein the method is conducted within a continuous furnace.

69. The method of claim 68 comprising conducting the steps of generating the radiation beam and detecting at least one property of the detectable species in a trough for receiving a pour from the furnace.

70. The method of claim 66 comprising converting a batch furnace to a continuous furnace and conducting the method within the furnace or in a trough outside the furnace.

* * * * *